US011999779B2

(12) United States Patent
Yednock et al.

(10) Patent No.: US 11,999,779 B2
(45) Date of Patent: Jun. 4, 2024

(54) ANTI-COMPLEMENT FACTOR C1q FAB FRAGMENTS AND USES THEREOF

(71) Applicant: Annexon, Inc., South San Francisco, CA (US)

(72) Inventors: Ted Yednock, Forest Knolls, CA (US); Sethu Sankaranarayanan, Fremont, CA (US); Michael Leviten, Emerald Hills, CA (US); Arnon Rosenthal, Woodside, CA (US)

(73) Assignee: Annexon, Inc., Brisbane, CA (US)

( * ) Notice: Subject to any disclaimer, the term of this patent is extended or adjusted under 35 U.S.C. 154(b) by 590 days.

(21) Appl. No.: 16/911,954

(22) Filed: Jun. 25, 2020

(65) Prior Publication Data
US 2020/0317765 A1    Oct. 8, 2020

Related U.S. Application Data

(62) Division of application No. 15/360,549, filed on Nov. 23, 2016, now Pat. No. 10,723,788.

(60) Provisional application No. 62/259,227, filed on Nov. 24, 2015.

(51) Int. Cl.
*C07K 16/18* (2006.01)
*G01N 33/564* (2006.01)
*G01N 33/68* (2006.01)

(52) U.S. Cl.
CPC .......... *C07K 16/18* (2013.01); *G01N 33/564* (2013.01); *G01N 33/6857* (2013.01); *G01N 33/6893* (2013.01); *C07K 2317/24* (2013.01); *C07K 2317/55* (2013.01); *C07K 2317/56* (2013.01); *C07K 2317/565* (2013.01); *C07K 2317/76* (2013.01); *C07K 2317/92* (2013.01); *G01N 2333/4716* (2013.01); *G01N 2800/50* (2013.01); *G01N 2800/7095* (2013.01)

(58) Field of Classification Search
None
See application file for complete search history.

(56) References Cited

U.S. PATENT DOCUMENTS

| | | |
|---|---|---|
| 6,197,930 B1 | 3/2001 | Sheppard et al. |
| 7,183,076 B2 | 2/2007 | Arathoon et al. |
| 8,025,878 B2 | 9/2011 | Gellerfors et al. |
| 8,148,330 B2 | 4/2012 | Barres et al. |
| 9,149,444 B2 | 10/2015 | Barres et al. |
| 9,382,313 B2 | 7/2016 | Barres et al. |
| 9,480,658 B2 | 11/2016 | Barres et al. |
| 9,493,555 B2 | 11/2016 | Barres et al. |
| 9,708,394 B2 | 7/2017 | Rosenthal et al. |
| 10,227,398 B2 | 3/2019 | Rosenthal et al. |
| 10,240,156 B2 | 3/2019 | Barres et al. |
| 10,316,081 B2 | 6/2019 | Rosenthal et al. |
| 10,330,671 B2 | 6/2019 | Barres et al. |
| 10,590,190 B2 | 3/2020 | Rosenthal et al. |
| 10,723,788 B2 | 7/2020 | Yednock et al. |
| 10,927,167 B2 | 2/2021 | Rosenthal et al. |
| 2002/0058311 A1 | 5/2002 | Browne et al. |
| 2002/0066117 A1 | 5/2002 | Nilsson et al. |
| 2002/0104104 A1 | 8/2002 | Games et al. |
| 2002/0160433 A1 | 10/2002 | Welch et al. |
| 2003/0170781 A1 | 9/2003 | Holloway et al. |
| 2003/0207336 A1 | 11/2003 | Jardieu et al. |
| 2004/0248156 A1 | 12/2004 | Hu et al. |
| 2005/0197285 A1 | 9/2005 | Rosen et al. |
| 2005/0214786 A1 | 9/2005 | Birse et al. |
| 2005/0241008 A1 | 10/2005 | Bredesen et al. |
| 2007/0135753 A1 | 6/2007 | Barres et al. |
| 2007/0269435 A1 | 11/2007 | Gillies et al. |
| 2008/0008719 A1 | 1/2008 | Bowdish et al. |
| 2008/0241145 A1 | 10/2008 | Goldenberg et al. |
| 2010/0143343 A1 | 6/2010 | Halstead et al. |
| 2011/0104156 A1 | 5/2011 | Christadoss et al. |
| 2012/0032860 A1 | 2/2012 | Suzuki et al. |
| 2012/0195880 A1 | 8/2012 | Barres et al. |
| 2012/0328601 A1 | 12/2012 | Barres et al. |
| 2013/0344073 A1 | 12/2013 | Schwaeble et al. |
| 2014/0140933 A1 | 5/2014 | Van Vlasselaer et al. |
| 2015/0259437 A1 | 9/2015 | Van Vlasselaer et al. |
| 2015/0368324 A1 | 12/2015 | Barres et al. |
| 2015/0368325 A1 | 12/2015 | Barres et al. |
| 2015/0368326 A1 | 12/2015 | Barres et al. |
| 2016/0159890 A1 | 6/2016 | Rosenthal et al. |
| 2016/0326237 A1 | 11/2016 | Rosenthal et al. |
| 2016/0355574 A1 | 12/2016 | Rosenthal et al. |
| 2016/0368973 A1 | 12/2016 | Rosenthal et al. |
| 2017/0152309 A1 | 6/2017 | Yednock et al. |
| 2017/0334976 A1 | 11/2017 | Rosenthal et al. |
| 2020/0239557 A1 | 7/2020 | Rosenthal et al. |

(Continued)

FOREIGN PATENT DOCUMENTS

| CN | 101657097 A | 2/2010 |
|---|---|---|
| CN | 101970484 A | 2/2011 |

(Continued)

OTHER PUBLICATIONS

Cho et al. Aging and Disease vol. 10, No. 3; pp. 652-663, Jun. 2019.*
Dejanovic et al. Nature Aging vol. 2; p. 837-850 Sep. 2022.*
Yednock et al. International Journal of Retina and Vitreous (2022) 8:79.*
Biomarkers Definitions Working Group; "Biomarkers and surrogate endpoints: Preferred definitions and conceptual framework," Clinical Pharmacology & Therapeutics, 69(3): 89-95 (2001).
D'Angelo et al., "Many Routes to an Antibody Heavy-Chain CDR3: Necessary, Yet Insufficient, for Specific Binding," Frontiers in Immunology, 9: Article 395 (2018).
Prince; "Biomarkers for diagnosing and monitoring autoimmune diseases," Biomarkers, 10(Supplement 1): S44-S49 (2005).

(Continued)

*Primary Examiner* — Sharon X Wen
(74) *Attorney, Agent, or Firm* — Foley Hoag LLP; David P. Halstead; Mohanad Mossalam

(57) ABSTRACT

The present disclosure relates generally to anti-C1q antibody Fab fragments and methods of using the same.

19 Claims, 3 Drawing Sheets

Specification includes a Sequence Listing.

(56) References Cited

U.S. PATENT DOCUMENTS

| | | |
|---|---|---|
| 2020/0317765 A1 | 10/2020 | Yednock et al. |
| 2021/0115119 A1 | 4/2021 | Rosenthal et al. |
| 2021/0277096 A1 | 9/2021 | Rosenthal et al. |

FOREIGN PATENT DOCUMENTS

| | | |
|---|---|---|
| CN | 102203610 A | 9/2011 |
| CN | 104011221 A | 8/2014 |
| EP | 1774972 A1 | 4/2007 |
| EP | 2266606 A1 | 12/2010 |
| EP | 3019240 A1 | 5/2016 |
| WO | WO-1985/02261 A1 | 5/1985 |
| WO | WO-1998/23761 A1 | 6/1998 |
| WO | WO-2003/052377 A2 | 6/2003 |
| WO | WO-2005/002513 A2 | 1/2005 |
| WO | WO-2005002512 A2 | 1/2005 |
| WO | WO-2005063816 A2 | 7/2005 |
| WO | WO-2007/070375 A2 | 6/2007 |
| WO | WO-2012/067267 A1 | 5/2012 |
| WO | WO-2012/163805 A1 | 12/2012 |
| WO | WO-2012/176765 A1 | 12/2012 |
| WO | WO-2013166604 A1 | 11/2013 |
| WO | WO-2014/066744 A2 | 5/2014 |
| WO | WO-2014/161570 A1 | 10/2014 |
| WO | WO-2014/169076 A1 | 10/2014 |
| WO | WO-2014/186599 A2 | 11/2014 |
| WO | WO-2014/186622 A2 | 11/2014 |
| WO | WO-2015/006504 A1 | 1/2015 |
| WO | WO-2015/006507 A1 | 1/2015 |
| WO | WO-2016/073685 A1 | 5/2016 |
| WO | WO-2017/091719 A1 | 6/2017 |
| WO | WO-2017/196874 A1 | 11/2017 |
| WO | WO-2018/017711 A1 | 1/2018 |
| WO | WO-2022034920 A1 | 2/2022 |
| WO | WO-2022/120137 A1 | 6/2022 |

OTHER PUBLICATIONS

Phieler et al., "The role of the complement system in metabolic organs and metabilic diseases," Seminars in Immunology, 25(1):47-53 (2013).

Stephan et al., "A dramatic increase of C1q protein in the CNS during normal aging," J Neurosci, 33(33):13460-13474 (2013).

Grover et al., "Pharmacokinetics and target engagement of intravitreal administration of ANX007, an anti-C1q antibody fragment, in nonhuman primates," Investigative Ophthalmology & Visual Science, 62: 219 (2021).

International Search Report and Written Opinion for International Application No. PCT/US2021/061755 dated Feb. 16, 2022.

Jiao et al., "Subretinal macrophages produce classical complement activator C1q leading to the progression of focal retinal degeneration," Molecular Neurodegeneration, 13(45): 1-18 (2018).

Reeck et al., "'Homology' in Proteins and Nucleic Acids: A Terminology Muddle and a Way out of it," Cell, 50: 667 (1987).

"Complement C1s antibody (49)," Product Data Sheet. ThermScientific. Pierce Antibody Products. 1995. pp. 1-2. Retrieved from the Internet: < http://www.pierce-antibodies.com/ <http://www.pierce-antibodies.com/> Complement-C1s-antibody-clone-49-monoclonal-ABS0024902.html#> on Sep. 23, 2014 (Sep. 23, 2014).

Angal et al., "A Single Amino Acid Substitution Abolishes the Heterogeneity of Chimeric Mouse/Human (IgG4) Antibody," Molecular Immunol, 30(1): 105-108 (1993).

Bigler et al., "Autoantibodies against complement C1q specifically target C1q bound on early apoptotic cells," Journal of Immunology, 183:3512-3521 (2009).

Brown et al., "Tolerance of single, but not multiple, amino acid replacements in antibody VH CDR 2: a means of minimizing B cell wastage from somatic hypermutation?" J Immunol, 156(9):3285-3291 (1996).

Carroll et al., "Antibody-mediates inhibition of human C1s and the classical complement pathway," Immunobiology, 218:1041-8 (2013).

Casset et al., "A peptide mimetic of an anti-CD4 monoclonal antibody by rational design," Biochemical and biophysical research communications, 307:198-205 (2003).

Chen et al., "Enhancement and Destruction of Antibody Function by Somatic Mutation: Unequal Occurrence is Controlled by V Gene Combinatorial Associations," EMBO J, 14: 2784-2794 (1995).

Chen et al., "Selection and analysis of an optimized anti-VEGF antibody: crystal structure of an affinity-matured Fab in complex with antigen," Journal of Molecular Biology, 293:865-881 (1999).

Colman, "Effects of Amino Acid Sequence Changes on Antibody-Antigen Interactions," Research in Immunology, 145: 33-36 (1994).

Extended European Search Report for EP Application No. 16869264.8 dated Jun. 27, 2019.

Extended European Search Report issued by the European Patent Office in corresponding Application No. EP 15857258.6, dated Mar. 20, 2018.

Gershoni et al., "Epitope mapping: the first step in developing epitope-based vaccines," BioDrugs, 21(3):145-156 (2007).

Hampel et al., "The future of Alzheimer's disease: the next 10 years," Prog Neurobiol, 95(4): 718-28 (Dec. 2011).

Hoekzema et al., "The Distortive Mechanism for the Activation of Complement Component C1 Supported by Studies with a Monoclonal Antibody against the "arms" of C1q," Mol Immunol, 25(5):485-494 (1988).

Hsiung et al., "A Monoclonal Antibody to C1q which Appears to Interact with C1r2C1s2-binding site," FEBS Letters, 229(1):21-24 (1988).

Hu et al., "Characterization of C1q in teleosts: insight into the molecular and functional evolution of C1q family and classical pathway," J Biol Chem, 285:28777-28786 (2010).

International Search Report and Written Opinion dated Apr. 2, 2015 from related PCT Application PCT/US14/038239.

International Search Report and Written Opinion dated Mar. 18, 2008 from related PCT Application PCT/US06/046857.

International Search Report and Written Opinion dated Nov. 7, 2014 from related PCT Application PCT/US14/038267.

International Search Report and Written Opinion dated Sep. 3, 2014 from related PCT Application PCT/US14/33560.

International Search Report and Written Opinion for International Application No. PCT/US2016/063587 dated Mar. 9, 2017.

International Search Report and Written Opinion for related PCT Application PCT/US2015/059185, dated Jan. 27, 2016.

International Search Report and Written Opinion from corresponding PCT Application PCT/US14/046042, dated Dec. 5, 2014.

International Search Report and Written Opinion from related PCT Application PCT/US14/046045, dated Nov. 4, 2014.

Kilchherr et al., "Activation of the First Component of Human Complement, C1, by Monoclonal Antibodies Directed Against Different Domains of Subcomponent C1q," J Immunol, 137(1): 255-262 (1986).

Kussie et al., "A Single Engineered Amino Acid Substitution Changes Antibody Fine Specificity," J Immunol, 152: 146-152 (1994).

Lamminmaki et al., "Crystal structure of a recombinant anti-estradiol Fab fragment in complex with 17ß-estradiol," Journal of Biological Chemistry, 276:36687-36694 (2001).

Liang et al., "Antinuclear Autoantibodies From B6. Sle1 Mice," p. 1, (2003).

Lopez-Requena et al., "Immunogenicity of autologous immunoglobulins: Principles and practices," Molecular Immunol, 44:3076-82 (2007).

MacCallum et al., "Antibody-antigen interactions: contact analysis and binding site topography," Journal of Molecular Biology, 262:732-745 (1996).

McGonigal, et al., "C1q-targeted inhibition of the classical complement pathway prevents injury in a novel mouse model of acute motor axonal neuropathy," Acta Neuropathologica Comm, 9(3): 729 (2016).

McGreer et al., "The future use of complement inhibitors for the treatment of neurological diseases," Drugs, 55(6):739-46 (1998).

Morgan et al., "The role of complement disorders of the nervous system," Immunopharmacology, 38:43-50 (1997).

(56) References Cited

OTHER PUBLICATIONS

Padlan et al., "Structure of an antibody-antigen complex: crystal structure of the HyHEL-10 Fab-lysozyme complex," PNAS, 86:5938-5942 (1989).

Pardridge et al., "Reengineering Biopharmaceuticals for Targeted Delivery Across the Blood-Brain Barrier," Methods in Enzymology, Academic Press, US, 503: 269-292 (Jan. 1, 2012).

Pascalis et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunology, 169: 3076-3084 (2002).

Pearson, "An Introduction to Sequence Similarity ("Homology") Searching," Current Protocols in Bioinformatics, 42(1):1-9 (2013).

Perrin et al., "Multimodal Techniques for Diagnosis and Prognosis of Alzheimer's disease," Nature, 461(7266): 916-922 (Oct. 15, 2009).

Phuan et al., "C1q-targeted monoclonal antibody prevents complement dependent cytotoxicity and neuropathology in in vitro and mouse models of neuromyelitis optica," Acta Neuropathol, 125(6):829-40 (2013).

Potlukova et al., "Complement component c1q and anti☐c1q antibodies in theory and in clinical practice," Scandinavian Journal of Immunology, 67:423-430 (2008).

Rader, "Overview on Concepts and Applications of Fab Antibody Fragments," Current Protocols in Protein Science, 6.9. 1-6.9. 14 (2009).

Reddy et al., "Elimination of Fc Receptor-Dependent Effector Functions of a Modified IgG4 Monoclonal Antibody to Human CD4," J Immunol, 164(4): 1925-1933 (2000).

Rodrigo et al., "Antibody Fragments and Their Purification by Protein L Affinity Chromatography," Antibodies, 4:259-277 (2015).

Roos et al., "Specific inhibition of the classical complement pathway by C1q-binding peptides," J Immunol, 167(12):7052-9 (2001).

Rudikoff et al., "Single Amino Acid Substitution Altering Antigen-Binding Specificity," Proc Natl Acad Sci USA, 79: 1979-1983 (1982).

Sahu et al., "Complement inhibitors: a resurgent concept in anti-inflammatory therapeutics," Immunopharmacology, 49(1-2):133-48 (2000).

Supplementary European Search Report for European Application No. EP 14 82 2330 dated Nov. 15, 2016.

Tradtrantip et al., "Enzymatic deglycosylation converts pathogenic neuromyelitis optica anti-aquaporin-4 IgG into therapeutic antibody," Ann Neurol, 73(1):77-85 (2013).

Tsumura et al., "Feasibility Study of the Fab Fragment of a Monoclonal Antibody Against Tissue Factor as a Diagnostic Tool," Int J Oncol, 47(6): 2107-2114 (2015).

Tuzun et al., "Targeting Classical Complement Pathway to Treat Complement Mediated Autoimmune Diseases," Current Topics in Complement II, Springer US, Jul. 26, 2008. p. 254-261 [online].

Vajdos et al., "Comprehensive functional maps of the antigen-binding site of an anti-ErbB2 antibody obtained with shotgun scanning mutagenesis," Journal of molecular biology, 320:415-428 (2002).

Veerhuis et al., "Complement in the brain," Molecular Immunology, 48:1592-1603 (2011).

Vickers, "A vaccine against Alzheimer's disease: developments to date," Drugs Aging, 19(7): 487-494 (2002).

Wu et al., "Humanization of a murine monoclonal antibody by simultaneous optimization of framework and CDR residues1," Journal of Molecular Biology, 294:151-162 (1999).

\* cited by examiner

A

B

ANTI-COMPLEMENT FACTOR C1q FAB FRAGMENTS AND USES THEREOF

CROSS-REFERENCE TO RELATED APPLICATIONS

This application is a divisional application of U.S. application Ser. No. 15/360,549, filed Nov. 23, 2016, which claims the benefit of U.S. Provisional Application Ser. No. 62/259,227, filed Nov. 24, 2015, which are both incorporated herein in their entirety by reference.

SEQUENCE LISTING

The instant application contains a Sequence Listing, which has been submitted via EFS-Web and is hereby incorporated by reference in its entirety. Said ASCII copy is named ANH-011 01 SL.txt and is 15,524 kilobytes in size.

BACKGROUND

Acute or chronic inflammation is a common component of many clinical disorders and the complement system has been associated with a growing number of inflammatory conditions that include degenerative diseases, cancer and transplant rejection. The complement system acts as a sensor of pathogens, recognizes diseased and damaged host cells, and closely collaborates with other immune and defense systems to eliminate potential danger. However, insufficient, excessive, or poorly controlled complement activation can tip the balance between health and disease and lead to self-attack on host cells. Such an immune imbalance may fuel a cycle between complement, inflammatory cells, and tissue damage that recreates inflammatory stimulators rather than resolving them and exacerbates clinical complications. Inappropriate activation of complement has been linked to many autoimmune, inflammatory, and neurodegenerative diseases, as well as ischemia-reperfusion injury and cancer. Therefore, therapeutic modulation of complement activity emerges as an attractive target for upstream inhibition of inflammatory processes.

SUMMARY

The present disclosure is generally directed to anti-C1q Fab fragments and uses thereof. Complement is a central component of the innate immune system, especially as it relates to inflammation and the body's defense against invading organisms. Complement is also involved in the clearance of self-antigens and apoptotic cells, forms a bridge to adaptive immunity, and also plays a significant role in tissue regeneration and tumor growth. To exercise these functions, the complement system relies on an interplay of soluble and cell-surface-bound proteins that interact with pathogen cell surfaces to mark them for destruction by phagocytes. The complement system is made up of a large number of distinct plasma proteins, primarily produced by the liver. A number of these proteins are a class of proteases known as zymogens, which are themselves activated by proteolytic cleavage. These zymogens may be widely distributed without being active until detecting a local pathogen. The complement system thus is activated through a triggered enzyme cascade.

Complement activation is initiated through three pathways: classical, alternative and lectin pathways. All three pathways are based on the detection of surface structures by pattern recognition proteins. In addition, all three pathways merge through a common intersection, complement C3. C3 is an acute phase reactant. The liver is the main site of synthesis, although small amounts are also produced by activated monocytes and macrophages. A single chain precursor (pro-C3) of approximately 200 kD is found intracellularly; the cDNA shows that it comprises 1,663 amino acids. This is processed by proteolytic cleavage into alpha and beta subunits which in the mature protein are linked by disulfide bonds. Pro-C3 contains a signal peptide of 22 amino acid residues, the beta chain (645 residues) and the alpha chain (992 residues). The 2 chains are joined by 4 arginine residues that are not present in the mature protein.

The classical pathway is activated by the binding of the complement protein C1q directly with patches of surface-bound antibodies (IgM and IgG), and also binding to C-reactive protein, serum amyloid P, pentraxin 3, and other ligands on the surface of apoptotic or microbial cells.

C1q is a large multimeric protein of 460 kDa consisting of 18 polypeptide chains (6 C1q A chains, 6 C1q B chains, and 6 C1q C chains). C1r and C1s complement proteins bind to the C1q tail region to form the C1 complex. Binding of the C1q complex to the surface of a cell or to the complement binding domain of an antibody Fc region induces a conformational change in C1q that leads to activation of an autocatalytic enzymatic activity in C1r, which then cleaves C1s to generate an active serine protease. Once activated, C1s cleaves C4, etc., leading to the complement cascade sequence. Ultimately this pathway leads to the formation of a membrane attack complex which lyses and kills the affected cell.

Complement is nonspecific in that it can attack both foreign invaders and host cells. Under normal conditions host cells, including neurons, are protected from potential complement-mediated damage by various fluid-phase and membrane-bound complement regulatory proteins, such as C1 inhibitor (C1-Inh). C1-INH dissociates C1r and C1s from the active C1 complex, which protects host cells from lysis or damage from the membrane attack complex. Other proteins that protect from potential complement-mediated damage include C4b-binding protein (C4BP), factor H (FH), complement receptor 1 (CR1; CD35), complement receptor Ig (CRIg), decay accelerating factor (DAF; CD55), membrane cofactor protein (MCP; CD46), and CD59. However, deficiencies of these components or excessive activation of complement in response to certain pathological conditions can overwhelm this protective mechanism. Such unbalanced activation has been associated with a growing number of diseases and pathological disorders.

For example, various complement components are expressed by neurons and glial cells in vitro and in vivo. While their function in the brain is unknown, the expression of many of these complement proteins is upregulated by serum or inflammatory cytokines after brain injury or during the course of neurodegenerative disease pathology. Astrocytes in culture have been reported to express C1q, C1r, C1s, C4, C2, and C3, as well as the more terminal proteins. Neurons have been reported to express C4 and C3. C1q was shown to be expressed in neuronal synapses and to mark these synapses for elimination. See, e.g., U.S. Patent Publication Nos. 2012/0195880 and 2012/328601. While selective synapse loss is an essential aspect of normal brain development ("synaptic pruning"), excessive synapse loss, especially in a mature or aging brain, results in neurodegeneration and cognitive decline. Elevated synaptic complement expression was found to contribute to synaptic loss in normal aging and in neurodegenerative disease progression. Conversely, lowering neuronal complement expression was found to be neuroprotective. Neurons affected by synapse loss may be central nervous system neurons, or peripheral system neurons. Based on these findings, neutralizing the activity of complement factors such as C1q is regarded as a promising therapeutic strategy to prevent synapse loss and to slow neurodegenerative disease progression as well as cognitive decline in normal aging. Neurodegenerative diseases involving synapse loss and considered to be amenable to treatments aiming at the neutralization of complement factors such as C1q include Alzheimer's disease, amyotrophic lateral sclerosis, multiple sclerosis, glaucoma, myotonic dystrophy, Down syndrome, Parkinson's disease, Huntington's disease, and the like.

In addition, the anaphylatoxin C5a has been shown to contribute to tumor growth in mice. In these situations where complement has deleterious effects, it is desirable to modulate its activation by using appropriate complement inhibitors. Currently, most complement inhibitors are protein drugs that are immunogenic and have poor tissue penetration. For example, the failure of the anti-05 mAb pexelizumab (Alexion Pharmaceuticals) use for the treatment of acute myocardial infarction may have been partly caused by its poor tissue penetration. In contrast to protein inhibitors, several low molecular weight drugs (under 2 kDa) have been used as complement inhibitors and do not suffer from the same disadvantages of protein inhibitors. However, many of the low molecular weight drugs and other small molecule inhibitors that have been reported, such as bisphenol disulfates, steroids and triterpenoids have generally had a low potency against complement. In addition, low molecular weight and small molecule complement inhibitors have other problems including poor selectivity and high toxicity. Another challenge for low molecular weight and small molecule complement inhibitors is that since the complement cascade relies on a large number of protein-protein interactions, the interaction surfaces are usually much larger compared to e.g. the pocket of enzymes, and amino acid residues involved in such interactions are often not contiguous. In addition, the contact surfaces are usually shallow and lack any grooves that would enable tight binding of small compounds. It is therefore telling that all the physiological complement regulators, including the protease inhibitor C1-Inh, are relatively large proteins. Despite the aforementioned challenges with protein-drug, low molecular weight, and small molecule complement inhibitors, antibody fragments (Fab) directed towards the inhibition of different components of the complement cascade may be advantageous for preventative, diagnostic, and therapeutic clinical applications. Such Fab molecules are desired in situations that require fast clearance, higher tissue penetration capability, absence of Fc-mediated effector functions (such as CDC, ADCC, and phagocytosis), and lower immunogenicity. In addition, Fab molecules do not form cross-linked immunocomplexes that can trigger anaphylaxis.

In certain aspects, the present disclosure provides an antibody Fab fragment that binds to a protein in the complement cascade. In some embodiments, the antibody Fab fragment binds to a C1q protein. In some embodiments, the antibody Fab fragment comprises a heavy chain and a light chain, wherein the heavy chain is truncated after the first heavy chain domain.

In preferred embodiments, the antibody Fab fragment is an anti-C1q antibody Fab fragment.

In some embodiments, the antibody Fab fragment may be prepared by any suitable method known in the art. For example, the antibody Fab fragment may be obtained from any whole antibody, especially a whole monoclonal antibody, using any suitable enzymatic cleavage and/or digestion techniques, such as treatment with the cysteine protease papain to yield an antibody Fab fragment.

In one embodiment, the antibody Fab fragment of the present invention is prepared by the use of recombinant DNA techniques involving the manipulation and re-expression of DNA encoding antibody variable and constant regions. Standard molecular biology techniques may be used to modify, add or delete further amino acids or domains as desired. Any alterations to the variable or constant regions are still encompassed by the terms 'variable' and 'constant' regions as used herein. Preferably, PCR is used to introduce a stop codon immediately following the codon encoding the interchain cysteine of $C_H1$, such that translation of the $C_H1$ domain stops at the interchain cysteine. Methods for designing suitable PCR primers are well known in the art and the sequences of antibody $C_H1$ domains are readily available. In some embodiments, stop codons may be introduced using site-directed mutagenesis techniques.

In some cases, the antibody Fab fragment starting material of the present invention may be derived from any antibody isotype ("class") including for example IgG, IgM, IgA, IgD and IgE and subclasses thereof, including for example IgG1, IgG2, IgG3 and IgG4. Preferably, the antibody Fab fragment of the present invention is derived from IgG1.

In some embodiments, the antibody Fab fragment starting material may be obtained from any species including for example mouse, rat, rabbit, pig, hamster, camel, llama, goat or human. In a preferred embodiment, the heavy and light chains of the antibody Fab fragment are from murine IgG1. Parts of the antibody Fab fragment may be obtained from more than one species. For example, the antibody fragments may be chimeric or humanized. In one example the constant regions are from one species and the variable regions from another. In another example, antibody Fab fragment is humanized.

The antibody fragment starting material may also be modified. In one example the variable region of the antibody fragment has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and optionally one or more framework amino acids from one antibody and the remainder of the variable region domain from a second antibody.

In some embodiments, the antibody Fab fragment comprises a heavy chain of the amino acid sequence provided in SEQ ID NO: 1 and a light chain of the amino acid sequence provided in SEQ ID NO:2. In some embodiments, the DNA sequence encoding the amino acids of SEQ ID NOs 1 and 2 are provided. In one embodiment, the nucleic acid sequence encoding SEQ ID NO: 1 is SEQ ID NO:3. In another embodiment, the nucleic acid sequence encoding SEQ ID NO:2 is SEQ ID NO:4.

Also disclosed are antibody Fab fragments wherein the heavy and light chains comprise a sequence having at least 90% identity or similarity to the sequences of SEQ ID NO:1 and SEQ ID NO:2, respectively. Preferably, the antibody Fab fragment comprises a heavy chain sequence having at least 90%, 95% or 98% identity or similarity to SEQ ID NO:1 and a light chain sequence having at least 90%, 95% or 98% identity or similarity to SEQ ID NO:2.

In some embodiments, the antibody Fab fragment binds specifically to human C1q, mouse C1q, dog C1q, rhesus C1q, cynomolgus monkey C1q or rat C1q. In some embodiments, the antibody Fab fragments binds specifically to both human C1q and mouse C1q. In some embodiments, the antibody Fab fragments binds specifically to both human C1q and rat C1q. In some embodiments, the antibody Fab fragments binds specifically to both human C1q and dog C1q. In some embodiments, the antibody Fab fragments binds specifically to both human C1q and rhesus C1q. In some embodiments, the antibody Fab fragments binds specifically to both human C1q and cynomolgus monkey C1q. In some embodiments, the antibody Fab fragments binds specifically to both mouse C1q and rat C1q. In some embodiments, the antibody Fab fragments binds specifically to both mouse C1q and dog C1q. In some embodiments, the antibody Fab fragments binds specifically to both mouse C1q and rhesus C1q. In some embodiments, the antibody Fab fragments binds specifically to both mouse C1q and cynomolgus monkey C1q. In some embodiments, the antibody Fab fragments binds specifically to both rat C1q and dog C1q. In some embodiments, the antibody Fab fragments binds specifically to both rat C1q and rhesus C1q. In some embodiments, the antibody Fab fragments binds specifically to both rat C1q and cynomolgus monkey C1q. In some embodiments, the antibody Fab fragments binds specifically to both dog C1q and rhesus C1q. In some embodiments, the antibody Fab fragments binds specifically to both dog C1q and cynomolgus monkey C1q. In some embodiments, the antibody Fab fragments binds specifically to rhesus dog C1q and cynomolgus monkey C1q. In some embodiments, the antibody Fab fragment binds to human C1q, mouse C1q and/or rat C1q, and at least one of the following: dog C1q, rhesus C1q, and cynomolgus monkey C1q.

In some embodiments, the antibody Fab fragment binds to both human C1q and mouse C1q. In other embodiments, the antibody Fab fragment binds to human C1q, mouse C1q, rat C1q, dog C1q, rhesus C1q, and cynomolgus monkey C1q.

In some embodiments, the antibody Fab fragment binds essentially the same C1q epitope as the antibody M1 produced by the hybridoma cell line with ATCC Accession Number PTA-120399. In some cases, the antibody Fab fragment inhibits the binding of the monoclonal antibody M1 produced by a hybridoma cell line with ATCC Accession Number PTA-120399 to human C1q or to mouse C1q.

In some embodiments, provided herein is a humanized anti-C1q antibody Fab fragment that binds to an epitope of C1q that is the same as or overlaps with the C1q epitope bound by another antibody of this disclosure. In certain embodiments, the humanized anti-C1q antibody Fab fragment that binds to an epitope of C1q is the same as or overlaps with the C1q epitope bound by anti-C1q antibody M1 produced by the hybridoma cell line with ATCC Accession Number PTA-120399. In some embodiments, the humanized anti-C1q antibody Fab fragment competes with another antibody of this disclosure for binding to C1q. In certain embodiments, the anti-C1q antibody Fab fragment competes with anti-C1q antibody M1 produced by the hybridoma cell line with ATCC Accession Number PTA-120399 or anti-C1q binding fragments thereof.

Since it is well-known in the art that antibody heavy and light chain CDR3 domains play a particularly important role in the binding specificity/affinity of an antibody for an antigen, the antibody Fab fragments of the present disclosure may comprise the heavy and light chain CDR3s of variable regions of the monoclonal antibody M1 produced by the hybridoma cell line having ATCC Accession Number PTA-120399. In some embodiments, the antibody Fab fragment further comprises the CDR2s of variable regions of the monoclonal antibody M1. In some embodiments, the antibody Fab fragment further comprises the CDRs of variable regions of the monoclonal antibody M1. In some embodiments, the antibody Fab fragment may further comprise any combinations of the CDRs.

In some embodiments, the antibody Fab fragment has been engineered to increase brain penetration. In some cases, the antibody Fab fragment has better brain penetration as compared to the corresponding full-length antibody.

In some embodiments, the antibody Fab fragment has only one binding site. In some embodiments, the antibody Fab fragment has the same affinity for C1q as the whole C1q antibody, incorporated herein by reference from U.S. Pat. No. 62/075,793. In some embodiments, the antibody Fab fragment inhibits proteins of the complement cascade, e.g., C1q, C4, C2, C3 convertase, C3a, C5, C3b, C5b, C6, C7, C8, and/or C9.

In some embodiments, the antibody fragment has a shorter half-life in human circulation as compared to its corresponding full-length antibody.

In some embodiments, the antibody Fab fragment is injected directly into the eye. In some embodiments, the antibody Fab fragment is injected into the eye for prevention or treatment of an ocular disease or condition and may be typically administered by ocular, intraocular, and/or intravitreal injection. Other methods administration by also be used, which includes but is not limited to, topical, parenteral, subcutaneous, intraperitoneal, intrapulmonary, intranasal, and intralesional administration. Parenteral infusions include intramuscular, intravenous, intra-arterial, intraperitoneal, or subcutaneous administration.

The antibody Fab fragments of the present invention are useful for the prevention and treatment complement-associated eye conditions (all eye conditions and diseases the pathology of which involves complement, including the classical and the alternative pathways), such as, for example, macular degenerative diseases, such as Chronic open-angle glaucoma, acute closed angle glaucoma, all stages of age-related macular degeneration (AMD), including dry and wet (non-exudative and exudative) forms (AMD-wet), Geographic atrophy, choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, retinal neovascularization, Leber's hereditary optic neuropathy, optic neuritis, Behcet's retinopathy, ischemic optic neuropathy, retinal vasculitis, ANCA vasculitis, Purtscher retinopathy, Sjogren's dry eye disease, dry AMD, sarcoidosis, temporal arteritis, polyarteritis nodosa, and multiple sclerosis.

A preferred group of complement-associated eye conditions includes age-related macular degeneration (AMD), including non-exudative (wet) and exudative (dry or atrophic) AMD, choroidal neovascularization (CNV), diabetic retinopathy (DR), and endophthalmitis.

In some embodiments, the antibody Fab fragment has a dissociation constant ($K_D$) for human C1q that ranges from 10 pM to 20 pM, or 1 pM to less than 10 pM. In some embodiments, the antibody Fab fragment has a dissociation constant ($K_D$) for mouse C1q that ranges from 1 pM to 200 pM. In some embodiments, the antibody Fab fragment specifically binds to and inhibits a biological activity of C1q. In some embodiments, the biological activity is (1) C1q binding to an autoantibody, (2) C1q binding to C1r, (3) C1q binding to C1s, (4) C1q binding to phosphatidylserine, (5)

C1q binding to pentraxin-3, (6) C1q binding to C-reactive protein (CRP), (7) C1q binding to globular C1q receptor (gC1qR), (8) C1q binding to complement receptor 1 (CR1), (9) C1q binding to beta-amyloid, (10) C1q binding to calreticulin (11) C1q binding to apoptotic cells, or (12) C1q binding to components of a nerve cell membrane.

In some embodiments, the biological activity is (1) activation of the classical complement activation pathway, (2) activation of antibody and complement dependent cytotoxicity, (3) CH50 hemolysis, (4) synapse loss, (5) B-cell antibody production, (6) dendritic cell maturation, (7) T-cell proliferation, (8) cytokine production (9) microglia activation, (10) Arthus reaction, (11) phagocytosis of synapses or nerve endings, or (12) activation of complement receptor 3 (CR3/C3) expressing cells.

In some embodiments, CH50 hemolysis comprises human, mouse, and/or rat CH50 hemolysis. In some embodiments, the antibody Fab fragment is capable of neutralizing from at least about 50%, to at least about 95% of CH50 hemolysis. In some embodiments, the antibody Fab fragment is capable of neutralizing at least 50% of CH50 hemolysis at a dose of less than 150 ng, less than 100 ng, less than 50 ng, or less than 20 ng. In some embodiments, the antibody Fab fragment binds C1q and inhibits biological function with a binding stoichiometry that ranges from less than 6:1 to 1:1, or less than 2:1 to 1:1.

In some embodiments, the antibody Fab fragment is humanized.

In other embodiment, the present disclosure provides for an isolated host cell comprising a nucleic acid sequence of any of the preceding embodiments. In some embodiments, the host comprises a cloning or expression vector comprising the nucleic acid sequences of the antibody Fab fragment. In some embodiments, the host cell is cultured containing the expression vector and nucleic acid in conditions suitable for expression of the antibody Fab fragment. In some embodiments, the antibody Fab fragment is subsequently recovered from the host cell (or host cell medium). Additionally, pharmaceutical compositions are provided containing anti-C1q antibody Fab fragments in combination with pharmaceutically acceptable carriers. The present disclosure also provides a kit containing an anti-C1q antibody Fab fragment for use in any of the methods described herein.

In some cases, the present disclosure provides for a method of treating or preventing a disease associated with complement activation in an individual in need of such treatment, the method comprising administering an anti-C1q antibody Fab fragment.

In some embodiments, the disease associated with complement activation is a neurodegenerative disorder. In some embodiments, the neurodegenerative disorder is associated with the loss of synapses or nerve connections, such as synapse loss that is dependent on the complement receptor 3(CR3)/C3 or complement receptor CR1. In some embodiments, the neurodegenerative disorder is associated with pathological activity-dependent synaptic pruning, synapse phagocytosis by microglia. In some embodiments, the neurodegenerative disorder is associated with Alzheimer's disease, amyotrophic lateral sclerosis, multiple sclerosis, glaucoma, myotonic dystrophy, Guillain-Barre' syndrome (GBS), Myasthenia Gravis, Bullous Pemphigoid, spinal muscular atrophy, Down syndrome, Parkinson's disease, and Huntington's disease.

In some embodiments, the disease associated with complement activation is an inflammatory disease, an autoimmune disease, or metabolic disorder selected from diabetes, obesity, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, Chronic open-angle glaucoma, acute closed angle glaucoma, macular degenerative diseases, age-related macular degeneration (AMD), (AMD-wet), Geographic atrophy choroidal neovascularization (CNV), uveitis, diabetic retinopathy, ischemia-related retinopathy, endophthalmitis, intraocular neovascular disease, diabetic macular edema, pathological myopia, von Hippel-Lindau disease, histoplasmosis of the eye, Neuromyelitis Optica (NMO), Central Retinal Vein Occlusion (CRVO), corneal neovascularization, retinal neovascularization, Leber's hereditary optic neuropathy, optic neuritis, Behcet's retinopathy, ischemic optic neuropathy, retinal vasculitis, ANCA vasculitis, Purtscher retinopathy, Sjogren's dry eye disease, dry AMD, sarcoidosis, temporal arteritis, polyarteritis nodosa, multiple sclerosis, allo-transplantation, hyperacute rejection, hemodialysis, chronic occlusive pulmonary distress syndrome (COPD), asthma, aspiration pneumonia, multiple sclerosis, Guillain-Barre syndrome, Myasthenia Gravis, Bullous Pemphigoid, or myositis. In some embodiments, the disease associated with complement activation is an autoimmune disease selected from myasthenia gravis, Diabetes mellitus type 1, Hashimoto's thyroiditis, Addison's disease, Coeliac disease, Crohn's disease, pernicious anaemia, Pemphigus vulgaris, vitiligo, autoimmune hemolytic anemias, paraneoplastic syndromes, a vasculitis disease, hypocomplementemic urticarial vasculitis (HUV), polymyalgia rheumatica, temporal arteritis, Wegener's granulomatosis, multiple sclerosis, Guillain-Barre syndrome, Myasthenia Gravis, Bullous Pemphigoid, or myositis.

In some embodiments, the present disclosure provides a method of detecting synapses in an individual, by a) administering an anti-C1q antibody Fab fragment to the individual, and b) detecting antibody Fab fragment bound to synapses, thereby detecting synapses in the individual. In some embodiments, the antibody Fab fragment bound to synapses is detected using imaging techniques selected from positron emission tomography (PET), X-ray computed tomography, single-photon emission computed tomography (SPECT), computed tomography (CT), and computed axial tomography (CAT). In some embodiments, the detection of antibody Fab fragment bound to synapses provides a quantitative measure of the number of synapses in the individual, such that the number of synapses in the individual is measured repeatedly over a period of time and a loss of synapses in the individual is detected over time and the loss of synapses over time is a measure for the efficacy of a treatment for the neurodegenerative disease or autoimmune disease.

In some embodiments, the present disclosure provides a method of detecting synapses in a biological sample, by a) contacting the biological sample with a humanized anti-C1q antibody Fab fragment, and b) detecting antibody Fab fragment bound to synapses, thereby detecting synapses in the individual. In some embodiments, the method further comprises a step before step a) of obtaining the biological sample from an individual. In some embodiments, the biological sample comprises a biopsy specimen, a tissue, or a cell. In some embodiments, the antibody Fab fragment is detected by immunofluorescence microscopy, immunocytochemistry, immunohistochemistry, ELISA, FACS analysis, immunoprecipitation, or micro-positron emission tomography.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In some embodiments, the antibody Fab fragments may be useful in the detection or treatment of many diseases or disorders, such as neurodegenerative disorders, such as neurodegenerative disorders, such as Alzheimer's disease, amyotrophic lateral sclerosis, multiple sclerosis, glaucoma, myotonic dystrophy, Guillain-Barre' syndrome (GBS), Myasthenia Gravis, Bullous Pemphigoid, spinal muscular atrophy, Down syndrome, Parkinson's disease, and Huntington's disease. In some embodiments, the antibody Fab fragments may be useful in the detection or treatment of inflammatory disease, autoimmune disease, or metabolic disorder, such as diabetes, obesity, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, Chronic open-angle glaucoma, acute closed angle glaucoma, macular degenerative diseases, age-related macular degeneration (AMD), (AMD-wet), Geographic atrophy choroidal neovascularization (CNV), uveitis, diabetic retinopathy, ischemia-related retinopathy, endophthalmitis, intraocular neovascular disease, diabetic macular edema, pathological myopia, von Hippel-Lindau disease, histoplasmosis of the eye, Neuromyelitis Optica (NMO), Central Retinal Vein Occlusion (CRVO), corneal neovascularization, retinal neovascularization, Leber's hereditary optic neuropathy, optic neuritis, Behcet's retinopathy, ischemic optic neuropathy, retinal vasculitis, ANCA vasculitis, Purtscher retinopathy, Sjogren's dry eye disease, dry AMD, sarcoidosis, temporal arteritis, polyarteritis nodosa, multiple sclerosis, allo-transplantation, hyperacute rejection, hemodialysis, chronic occlusive pulmonary distress syndrome (COPD), asthma, aspiration pneumonia, myasthenia gravis, Diabetes mellitus type 1, Hashimoto's thyroiditis, Addison's disease, Coeliac disease, Crohn's disease, pernicious anaemia, Pemphigus vulgaris, vitiligo, autoimmune hemolytic anemias, paraneoplastic syndromes, a vasculitis disease, hypocomplementemic urticarial vasculitis (HUV), polymyalgia rheumatica, temporal arteritis, Wegener's granulomatosis or multiple sclerosis, Guillain-Barre syndrome, Myasthenia Gravis, Bullous Pemphigoid, or myositis.

In some embodiments, methods are provided for protecting or treating an individual suffering from adverse effects of synapse loss. These findings have broad implications for a variety of clinical conditions, including neurodegenerative conditions involving synaptic loss, which conditions may include Alzheimer's disease; amyotrophic lateral sclerosis; multiple sclerosis, glaucoma, myotonic dystrophy, Down syndrome; Parkinson's disease, Huntington's disease; and the like. The loss of synapses is inhibited by contacting neurons with agents that block complement, including specific components, such as C1q.

In some embodiments, a method is provided of determining a subject's risk of developing a disease associated with complement activation, comprising: (a) administering an anti-C1q antibody fragment to the subject, wherein the antibody fragment is coupled to a detectable label; (b) detecting the detectable label to measure the amount or location of C1q in the subject; and (c) comparing the amount or location of C1q to a reference, wherein the risk of developing a disease associated with complement activation is characterized based on the comparison of the amount of C1q as compared to the reference.

In some embodiments, the detectable label comprises a nucleic acid, oligonucleotide, enzyme, radioactive isotope, biotin, or a fluorescent label. In some embodiments, the antibody is labeled with a coenzyme such as biotin using the process of biotinylation. When biotin is used as a label, the detection of the antibody is accomplished by addition of a protein such as avidin or its bacterial counterpart streptavidin, either of which can be bound to a detectable marker such as the aforementioned dye, a fluorescent marker such as fluorescein, a radioactive isotope or an enzyme such as peroxidase.

In some embodiments, the detectable label is detected using an imaging agent for x-ray, CT, MRI, ultrasound, PET and SPECT.

In some embodiments, the fluorescent label is selected from fluorescein, rhodamine, cyanine dyes or BODIPY.

In some embodiments, a method is provided of reducing a subject's risk of developing a disease associated with complement activation, comprising administering an anti-C1q antibody fragment, wherein the anti-C1q antibody fragment prevents or reduces the risk of developing a disease associated with complement activation, thereby preventing or reducing the risk of future diseases associated with complement activation.

In some embodiments, the antibody Fab fragment has a shorter half-life as compared to its corresponding full-length antibody.

DESCRIPTION OF THE FIGURES

FIG. 1 shows that the M1 Fab has the same binding affinity as the M1 whole antibody. FIG. 1A shows an ELISA measuring antibody binding to C1q (anti-kappa light chain detection). FIG. 1B is an image showing M1 whole antibody (bivalent) and M1 Fab (monovalent).

FIG. 2 shows a standard functional measure of C1q activity inhibition of RBC lysis.

DETAILED DESCRIPTION

Figure 1:
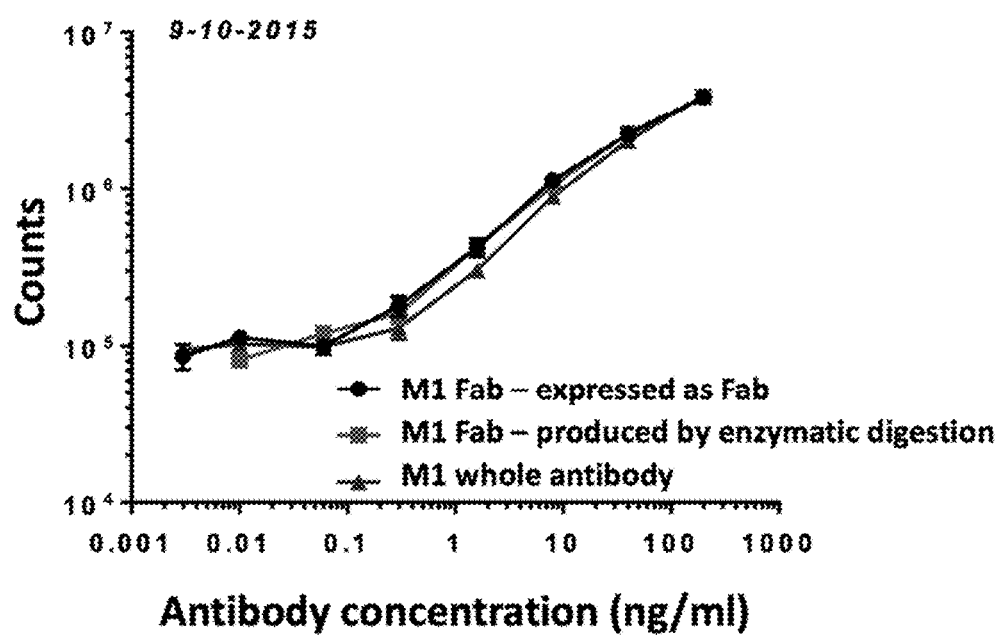
FIG. 1 consists of two panels, (A) and (B).
Figure 1:
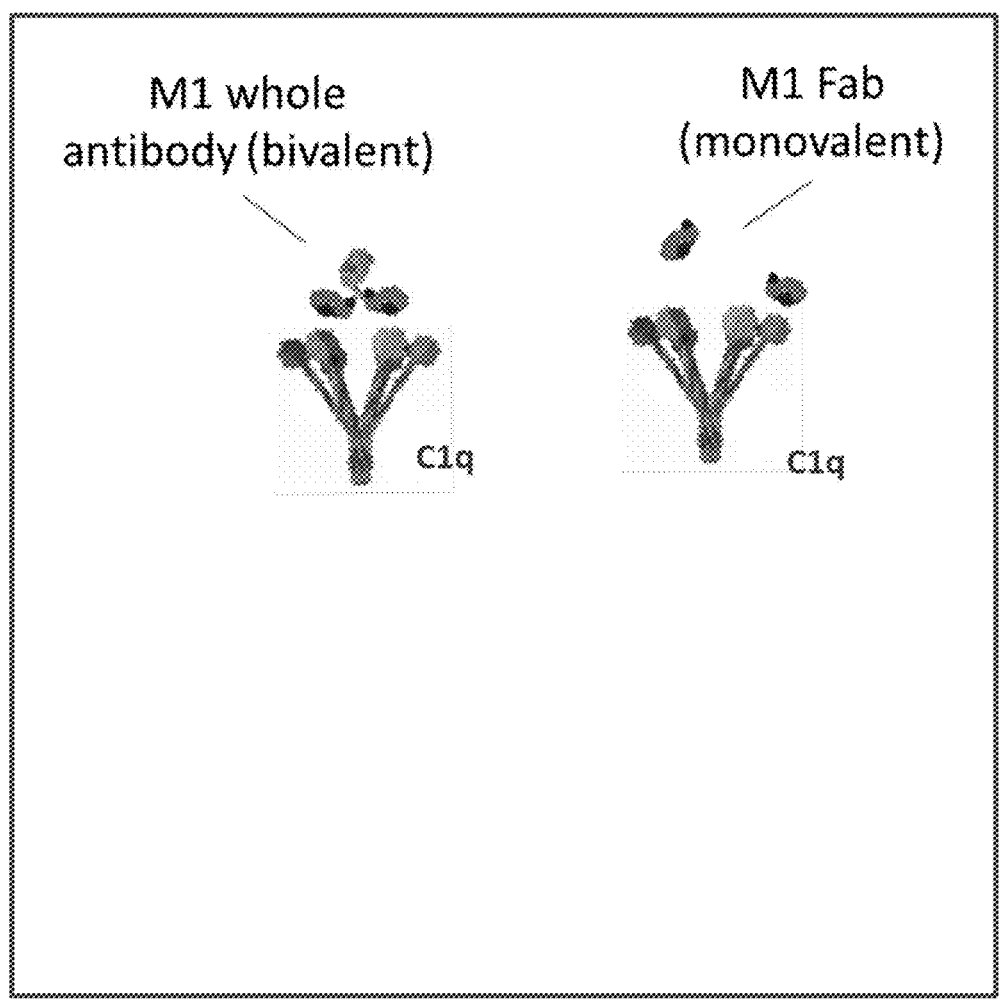

Polyclonal and monoclonal antibodies are naturally generated as immunoglobulin (Ig) molecules in the immune system's response to a pathogen. A dominating format with a concentration of 8 mg/ml in human serum, the ~150-kDa IgG1 molecule is composed of two identical ~50-kDa heavy chains and two identical ~25-kDa light chains.

Before the advent of recombinant DNA technology, proteolytic enzymes (proteases) that cleave polypeptide sequences have been used to dissect the structure of antibody molecules and to determine which parts of the molecule are responsible for its various functions. Limited digestion with the protease papain cleaves antibody molecules into three fragments. Two fragments, known as Fab fragments, are identical and contain the antigen-binding activity. The Fab fragments correspond to the two identical arms of the antibody molecule, each of which consists of a complete light chain paired with the $V_H$ and $C_H1$ domains of a heavy chain. The other fragment contains no antigen binding activity but was originally observed to crystallize readily, and for this reason was named the Fc fragment (Fragment crystallizable). When Fab molecules were compared to IgG molecules, it was found that Fab are superior to IgG for certain in vivo applications due to their higher mobility and tissue penetration capability, their reduced circulatory half-life, their ability to bind antigen monovalently without mediating antibody effector functions, and their lower immunogenicity.

The Fab molecule is an artificial ~50-kDa fragment of the Ig molecule with a heavy chain shortened by constant domains $C_H2$ and $C_H3$. Two heterophilic ($V_L$-$V_H$ and $C_L$-$C_H1$) domain interactions underlie the two-chain structure of the Fab molecule, which is further stabilized by a disulfide bridge between $C_L$ and $C_H1$. Fab and IgG have identical antigen binding sites formed by six complementarity-determining regions (CDRs), three each from $V_L$ and $V_H$ (LCDR1, LCDR2, LCDR3 and HCDR1, HCDR2, HCDR3). The CDRs define the hypervariable antigen binding site of antibodies. The highest sequence variation is found in LCDR3 and HCDR3, which in natural immune systems are generated by the rearrangement of $V_L$ and $J_L$ genes or VH, $D_H$ and $J_H$ genes, respectively. LCDR3 and HCDR3 typically form the core of the antigen binding site. The conserved regions that connect and display the six CDRs are referred to as framework regions. In the three-dimensional structure of the variable domain, the framework regions form a sandwich of two opposing antiparallel β-sheets that are linked by hypervariable CDR loops on the outside and by a conserved disulfide bridge on the inside. This unique combination of stability and versatility of the antigen binding site of Fab and IgG underlie its success in clinical practice for the diagnosis, monitoring, prevention, and treatment of disease.

In certain embodiments, the present disclosure provides an anti-C1q antibody Fab fragment that binds to a C1q protein comprising a heavy ($V_H$/$C_H1$) and light chain ($V_L$/$C_L$), wherein the anti-C1q antibody Fab fragment has six complementarity determining regions (CDRs), three each from $V_L$ and VH (HCDR1, HCDR2, HCDR3, and LCDR1, LCDR2, LCDR3). The heavy chain of the antibody Fab fragment is truncated after the first heavy chain domain of IgG1 (SEQ ID NO:1), and comprises the following amino acid sequence:

QVQLVQSGAELKKPGASVKVSCKSSGYHFTSYWMHWVKQAPGQGLEWIGV

IHPNSGSINYNEKFESRVTITVDKSTSTAYMELSSLRSEDTAVYYCAGER

DSTEVLPMDYWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHT

The complementarity determining regions (CDRs) of SEQ ID NO:1 are depicted in bolded and underlined text.

The nucleotide sequence corresponding to SEQ ID NO:1 is SEQ ID NO:3:

CAGGTGCAGCTGGTGCAGTCAGGGGCTGAGCTGAAGAAGCCTGGGGCTTC

AGTGAAGGTTTCCTGCAAGTCTTCTGGCTACCATTTCACCAGCTACTGGA

TGCACTGGGTGAAGCAGGCCCCTGGACAAGGCCTTGAGTGGATTGGAGTG

ATTCATCCTAATAGTGGTAGTATTAACTACAATGAGAAGTTCGAGAGCAG

AGTCACAATTACTGTAGACAAATCCACCAGCACAGCCTACATGGAGCTCA

GCAGCCTGAGATCTGAGGACACGGCGGTCTATTATTGTGCAGGAGAGAGA

GATTCTACGGAGGTTCTCCCTATGGACTACTGGGGTCAAGGAACCACGGT

CACCGTCTCCTCAGCGTCCACCAAAGGCCCGTCCGTGTTTCCGCTGGCGC

CGTCCTCCAAATCCACCTCCGGCGGCACCGCGGCGCTGGGCTGCCTGGTG

AAAGATTATTTTCCGGAACCGGTGACCGTGTCCTGGAATTCCGGCGCGCT

GACCTCCGGCGTGCATACCTTTCCGGCGGTGCTGCAGTCCTCCGGCCTGT

ATTCCCTGTCCTCCGTGGTGACCGTGCCGTCCTCCTCCCTGGGCACCCAG

ACCTATATTTGCAATGTGAATCATAAACCGTCCAATACCAAAGTGGATAA

AAAAGTGGAACCGAAATCCTGCGATAAAACCCATACC

The complementarity determining regions (CDRs) of SEQ ID NO:3 are depicted in bolded and underlined text.

The light chain domain of the antibody Fab fragment comprises the following amino acid sequence (SEQ ID NO:2):

DVQITQSPSSLSASLGERATINCRASKSINKYLAWYQQKPGKAPKLLIYS

GSTLQSGIPARFSGSGSGTDFTLTISSLEPEDFAMYYCQQHNEYPLTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The complementarity determining regions (CDRs) of SEQ ID NO:2 are depicted in bolded and underlined text.

The nucleotide sequence corresponding to SEQ ID NO:2 is SEQ ID NO:4:

GATGTCCAGATCACACAGTCTCCATCTTCCCTTTCTGCATCTCTCGGAGA

AAGAGCTACTATTAATTGCAGGGCAAGTAAGAGCATTAACAAATACTTAG

CCTGGTATCAACAGAAACCTGGGAAAGCTCCTAAGCTCCTTATCTACTCT

-continued

```
GGCTCCACTTTGCAATCTGGAATTCCAGCAAGGTTCAGTGGCAGTGGATC

TGGTACAGATTTCACTCTCACCATCAGTAGCCTGGAGCCTGAAGATTTTG

CAATGTATTACTGTCAACAACATAATGAATACCCGCTCACGTTCGGTCAG

GGGACCAAGCTGGAGATCAAACGAACTGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG

CAGACTACGAGAAACACAAAGTCTACGCCTGCGAAGTCACCCATCAGGGC

CTGAGCTCGCCCGTCACAAAGAGCTTCAACAGGGGAGAGTGTTAG
```

The complementarity determining regions (CDRs) of SEQ ID NO:4 are depicted in bolded and underlined text.

The amino acid sequence corresponding to SEQ ID NO:5 is:

```
                                    (SEQ ID NO: 5)
QVQLVQSGAELKKPGASVKVSCKSSGYHFTSYWMHWVKQAPGQGLEWIGV

IHPNSGSINYNEKFESKATITVDKSTSTAYMQLSSLTSEDSAVYYCAGER

DSTEVLPMDYWGQGTSVTVSS.
```

The complementarity determining regions (CDRs) of SEQ ID NO:5 are depicted in bolded and underlined text.

The amino acid sequence corresponding to SEQ ID NO:6 is:

```
                                    (SEQ ID NO: 6)
QVQLVQSGAELKKPGASVKVSCKSSGYHFTSYWMHWVKQAPGQGLEWIGV

IHPNSGSINYNEKFESRATITVDKSTSTAYMELSSLRSEDTAVYYCAGER

DSTEVLPMDYWGQGTTVTVSS.
```

The complementarity determining regions (CDRs) of SEQ ID NO:6 are depicted in bolded and underlined text.

The amino acid sequence corresponding to SEQ ID NO:7 is:

```
                                    (SEQ ID NO: 7)
QVQLVQSGAELKKPGASVKVSCKSSGYHFTSYWMHWVKQAPGQGLEWIGV

IHPNSGSINYNEKFESRVTITVDKSTSTAYMELSSLRSEDTAVYYCAGER

DSTEVLPMDYWGQGTTVTVSS.
```

The complementarity determining regions (CDRs) of SEQ ID NO:7 are depicted in bolded and underlined text.

The amino acid sequence corresponding to SEQ ID NO:8 is:

```
                                    (SEQ ID NO: 8)
QVQLVQSGAELKKPGASVKVSCKSSGYHFTSYWMHWVRQAPGQGLEWIGV

IHPNSGSINYNEKFESRVTITVDKSTSTAYMELSSLRSEDTAVYYCAGER

DSTEVLPMDYWGQGTTVTVSS.
```

The complementarity determining regions (CDRs) of SEQ ID NO:8 are depicted in bolded and underlined text.

The amino acid sequence corresponding to SEQ ID NO:9 is:

```
                                    (SEQ ID NO: 9)
DVQITQSPSYLAASLGERATINCRASKSINKYLAWYQQKPGKTNKLLIYS

GSTLQSGIPARFSGSGSGTDFTLTISSLEPEDFAMYYCQQHNEYPLTFGQ

GTKLEIK.
```

The complementarity determining regions (CDRs) of SEQ ID NO:9 are depicted in bolded and underlined text.

The amino acid sequence corresponding to SEQ ID NO:10 is:

```
                                    (SEQ ID NO: 10)
DVQITQSPSSLSASLGERATINCRASKSINKYLAWYQQKPGKANKLLIYS

GSTLQSGIPARFSGSGSGTDFTLTISSLEPEDFAMYYCQQHNEYPLTFGQ

GTKLEIK.
```

The complementarity determining regions (CDRs) of SEQ ID NO:10 are depicted in bolded and underlined text.

The amino acid sequence corresponding to SEQ ID NO:11 is:

```
                                    (SEQ ID NO: 11)
DVQITQSPSSLSASLGERATINCRASKSINKYLAWYQQKPGKAPKLLIYS

GSTLQSGIPARFSGSGSGTDFTLTISSLEPEDFAMYYCQQHNEYPLTFGQ

GTKLEIK.
```

The complementarity determining regions (CDRs) of SEQ ID NO:11 are depicted in bolded and underlined text.

The amino acid sequence corresponding to SEQ ID NO:12 is:

```
                                    (SEQ ID NO: 12)
DIQLTQSPSSLSASLGERATINCRASKSINKYLAWYQQKPGKAPKLLIYS

GSTLQSGIPARFSGSGSGTDFTLTISSLEPEDFAMYYCQQHNEYPLTFGQ

GTKLEIK.
```

The complementarity determining regions (CDRs) of SEQ ID NO:12 are depicted in bolded and underlined text.

Methods are provided for protecting or treating an individual suffering from adverse effects of synapse loss. It is shown herein that immature astrocytes in normal development produce a signal that induces neurons to express specific complement proteins, thus enabling a developmental window during which synapse elimination occurs. Expression of these proteins in development mirrors the period of developmental synaptogenesis, being off in embryonic brain and adult brain but on at high levels in postnatal brain.

These findings have broad implications for a variety of clinical conditions, particularly neurodegenerative conditions where synapse loss is involved. Synapse loss is inhibited by contacting neurons with inhibitors or antagonists of the complement pathway. For example, inhibitors can block activation of the complement cascade, can block the expression of specific complement proteins in neurons, can interfere with signaling molecules that induce complement activation, can upregulate expression of complement inhibitors in neurons, and otherwise interfere with the role of complement in synapse loss. The ability to prevent synapse loss, e.g. in adult brains, has important implications for maintaining normal neuronal function in a variety of neurodegenerative conditions.

Definitions

As used herein the specification, "a" or "an" may mean one or more. As used herein in the claim(s), when used in conjunction with the word "comprising", the words "a" or "an" may mean one or more than one. For example, reference to an "antibody" is a reference to from one to many antibodies, and includes equivalents thereof known to those skilled in the art, and so forth. As used herein "another" may mean at least a second or more.

The term "preventing" is art-recognized, and when used in relation to a condition, such as an epilepsy disease, is well understood in the art, and includes administration of a composition which reduces the frequency or severity, or delays the onset, of one or more symptoms of the medical condition in a subject relative to a subject who does not receive the composition. Thus, the prevention of epilepsy disease progression includes, for example, slowing or halting the average amount of neurodegeneration in a population of patients receiving a therapy relative to a control population that did not receive the therapy, e.g., by a statistically and/or clinically significant amount. Similarly, the prevention of neurodegenerative disease progression includes reducing the likelihood that a patient receiving a therapy will develop a disability, such as cognitive decline and/or memory loss, or delaying the onset of disability, relative to a patient who does not receive the therapy.

The term "subject" as used herein refers to a living mammal and may be interchangeably used with the term "patient". Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender.

As used herein, the term "treating" or "treatment" includes reducing, arresting, or reversing the symptoms, clinical signs, or underlying pathology of a condition to stabilize or improve a subject's condition or to reduce the likelihood that the subject's condition will worsen as much as if the subject did not receive the treatment.

The term "therapeutically effective amount" of a compound with respect to the subject method of treatment refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. A therapeutically effective amount herein may vary according to factors such as the disease state, age, sex, and weight of the patient, and the ability of the antibody to elicit a desired response in the individual.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

"Chronic" administration refers to administration of the medicament(s) in a continuous as opposed to acute mode, so as to maintain the initial therapeutic effect (activity) for an extended period of time. "Intermittent" administration refers to treatment that is not administered consecutively without interruption, but rather is cyclic/periodic in nature.

As used herein, administration "conjointly" with another compound or composition includes simultaneous administration and/or administration at different times. Conjoint administration also encompasses administration as a co-formulation or administration as separate compositions, including at different dosing frequencies or intervals, and using the same route of administration or different routes of administration.

Synapse loss. Synapses are asymmetric communication junctions formed between two neurons, or, at the neuromuscular junction (NMJ) between a neuron and a muscle cell. Chemical synapses enable cell-to-cell communication via secretion of neurotransmitters, whereas in electrical synapses signals are transmitted through gap junctions, specialized intercellular channels that permit ionic current flow. In addition to ions, other molecules that modulate synaptic function (such as ATP and second messenger molecules) can diffuse through gap junctional pores. At the mature NMJ, pre- and postsynaptic membranes are separated by a synaptic cleft containing extracellular proteins that form the basal lamina. Synaptic vesicles are clustered at the presynaptic release site, transmitter receptors are clustered in junctional folds at the postsynaptic membrane, and glial processes surround the nerve terminal.

Synaptogenesis is a dynamic process. During development, more synapses are established than ultimately will be retained. Therefore, the elimination of excess synaptic inputs is a critical step in synaptic circuit maturation. Synapse elimination is a competitive process that involves interactions between pre- and postsynaptic partners. In the CNS, as with the NMJ, a developmental, activity-dependent remodeling of synaptic circuits takes place by a process that may involve the selective stabilization of coactive inputs and the elimination of inputs with uncorrelated activity. The anatomical refinement of synaptic circuits occurs at the level of individual axons and dendrites by a dynamic process that involves rapid elimination of synapses. As axons branch and remodel, synapses form and dismantle with synapse elimination occurring rapidly.

In addition to the normal developmental loss, synapse loss is an early pathological event common to many neurodegenerative disorders, and is the best correlate to the cognitive impairment. Studies in the brains of patients with pre-clinical Alzheimer's disease (AD), as well as in transgenic animal models have shown that synaptic damage occurs early in disease progression. This early disruption of synaptic connections in the brain results in neuronal dysfunction that, in turn, leads to the characteristic symptoms of dementia and/or motor impairment observed in several neurodegenerative disorders.

Several molecules involved in AD and other neurodegenerative disorders play an important role in synaptic function. For example, AβPP has a preferential localization at central and peripheral synaptic sites. In transgenic mice, abnormal expression of mutant forms of AβPP results not only in amyloid deposition, but also in widespread synaptic damage.

This synaptic pathology occurs early and is associated with levels of soluble Aβ1-42 rather than with plaque formation. Other neurodegenerative diseases where gene products have been shown to be closely associated with synaptic complexes include Huntington's disease (HD) and myotonic dystrophy (DM). Huntingtin is a membrane-bound protein with a distribution very similar to that of synaptic vesicle protein synaptophysin. Studies in human brain detected htt in perikarya of some neurons, neuropil, varicosities and as punctate staining likely to be nerve endings. The serine/threonine kinase (DMK), which is the gene product of the DM gene, has been found to localize post-synaptically at the neuromuscular junction of skeletal muscle and at intercalated discs of cardiac tissue. DMK was also found at synaptic sites in the cerebellum, hippocampus, midbrain and medulla.

Inhibiting synapse loss results in maintenance or reduced loss of synapses, where a decrease would otherwise occur. By "modulation" of synapse loss as used herein, it is meant that the number of synapses lost is either enhanced or suppressed as required in the specific situation. As used herein, the term "modulator of synapse loss" refers to an agent that is able to alter synapse loss. Modulators include, but are not limited to, both "activators" and "inhibitors". An "activator" or "agonist" is a substance that enhances synapse loss. Conversely, an "inhibitor" or "antagonist" decreases synapse loss. The reduction may be complete or partial. As used herein, modulators include, without limitation, C1q antagonists and agonists.

Agonists and antagonists may include proteins, nucleic acids, carbohydrates, antibodies, or any other molecules that decrease the effect of a protein. The term "analog" is used herein to refer to a molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry.

Complement. Complement is a system of plasma proteins that interacts with the cell surfaces of pathogens or cells to mark them for destruction by phagocytes. The complement system is made up of a large number of distinct plasma proteins, primarily produced by the liver. A number of these proteins are a class of proteases, called zymogens, which are themselves activated by proteolytic cleavage. These zymogens can thus be widely distributed without being active until activated by a local pathogen. The complement system thus is activated through a triggered enzyme cascade.

The classical pathway is activated by the binding of the complement protein C1q directly to the cell surface or to an antibody that is bound to the cell surface. C1q is a large multimeric protein of 460 kDa consisting of 18 polypeptide chains (6 C1q A chains, 6 C1q B chains, and 6 C1q C chains). C1r and C1s complement proteins to bind to the C1q tail region to form the C1 complex. Binding of the C1q complex to the surface of a cell or to the complement binding domain of an antibody Fc region induces a conformational change in C1q that leads to activation of an autocatalytic enzymatic activity in C1r, which then cleaves C1s to generate an active serine protease. Once activated, C1s cleaves C4, etc., leading to the complement cascade sequence. Ultimately this pathway leads to the formation of a membrane attack complex which lyses and kills the affected cell. Normal cells, including neurons, express molecules such as CD59 that protect them from lysis or damage from the membrane attack complex and the C1 inhibitor (C1-INH) which dissociates C1 rand C1 s from the active C1 complex.

Various complement proteins are expressed by neurons and glial cells in vitro and in vivo. Their function in the brain is unknown. The expression of many of these complement proteins is upregulated by serum or inflammatory cytokines or after brain injury. Astrocytes in culture have been reported to express C1q, C1r, C1s, C4, C2, and C3, as well as the more terminal proteins. Neurons have been reported to express C4 and C3, but only to express C1q after brain injury.

Three pathways have been elucidated through which the complement cascade can be initiated; classical, alternative and lectin Pathways. All three pathways merge through at common intersection, complement C3. C3 is an acute phase reactant. The liver is the main site of synthesis, although small amounts are also produced by activated monocytes and macrophages. A single chain precursor (pro-C3) of approximately 200 kD is found intracellularly; the eDNA shows that it comprises 1,663 amino acids. This is processed by proteolytic cleavage into alpha and beta subunits which in the mature protein are linked by disulfide bonds. Pro-C3 contains a signal peptide of 22 amino acid residues, the beta chain (645 residues) and the alpha chain (992 residues). The 2 chains are joined by 4 arginine residues that are not present in the mature protein. In the alternative pathway complement C3 undergoes spontaneous cleavage resulting in complement B binding to C3b. Diffusion of the Ba subunit results in an active alternative pathway C3 convertase (C3bBb). C3bBb is stabilized by binding to properdin prior to merging.

Inhibition of complement. A number of molecules are known that inhibit the activity of complement. In addition to known compounds, suitable inhibitors can be screened by methods described herein. As described above, normal cells can produce proteins that block complement activity, e.g., CD59, C1 inhibitor, etc. In some embodiments of the invention, complement is inhibited by upregulating expression of genes encoding such polypeptides.

Modifications of molecules that block complement activation are also known in the art. Such molecules include, without limitation, modified complement receptors, such as soluble CR1. The mature protein of the most common allotype of CR1 contains 1998 amino acid residues: an extracellular domain of 1930 residues, a transmembrane region of 25 residues, and a cytoplasmic domain of 43 residues. The entire extracellular domain is composed of 30 repeating units referred to as short consensus repeats (SCRs) or complement control protein repeats (CCPRs), each consisting of 60 to 70 amino acid residues. Recent data indicate that C1q binds specifically to human CR1. Thus, CR1 recognizes all three complement opsonins, namely C3b, C4b, and C1q. A soluble version of recombinant human CR1 (sCR1) lacking the transmembrane and cytoplasmic domains has been produced and shown to retain all the known functions of the native CR1. The cardioprotective role of sCR1 in animal models of ischemia/reperfusion injury has been confirmed. Several types of human C1q receptors (C1qR) have been described. These include the ubiquitously distributed 60- to 67-kDa receptor, referred to as cC1qR because it binds the collagen-like domain of C1q. This C1qR variant was shown to be calreticulin; a 126-kDa receptor that modulates monocyte phagocytosis. gC1qR is not a membrane-bound molecule, but rather a secreted soluble protein with affinity for the globular regions of C1q, and may act as a fluid-phase regulator of complement activation.

Decay accelerating factor (OAF) (CD55) is composed of four SCRs plus a serine/threonine-enriched domain that is capable of extensive O-linked glycosylation. OAF is attached to cell membranes by a glycosyl phosphatidyl inositol (GPI) anchor and, through its ability to bind C4b and C3b, it acts by dissociating the C3 and C5 convertases. Soluble versions of OAF (sDAF) have been shown to inhibit complement activation.

C1 inhibitor, a member of the "serpin" family of serine protease inhibitors, is a heavily glycosylated plasma protein that prevents fluid-phase C1 activation. C1 inhibitor regulates the classical pathway of complement activation by blocking the active site of C1r and C1s and dissociating them from C1q.

Peptide inhibitors of complement activation include C5a (van Oostrum et al., 1996); C5a C-terminal octapeptides (Kawai et al., 1992); C5a His67-modified C-terminal octapeptide analogues (Or et al., 1992); C089 (C5a hexapeptide, Konteatis et al., 1994); C3a C-terminus (Kretzschmar et al., 1992); Factor B-related hexapeptides (Lesavre et al., 1982); C1q B chain helical region (Fryer et al., 1997); DFP (Diisopropyl fluorophosphates, Cole et al., 1997); BCX-14 70 (K-76 analog, Kaufman et al., 1995); TKIX (K-76 derivative) Sindelar et al. 1996); K-76 derivative, Tanaka 1996); FUT-175 (nafamostat mesilate, Inose et al. 1997).

Other inhibitory molecules include Fucan (Charreau et al., 1997); Complestatin (Momota et al., 1991); Decorin (Krumdieck et al., 1992); heparin (te Velthuis et al., 1996); LU 1198 (Gralinski et al., 1997); CSPG (Kirschfink et al., 1997); L-156,602 (Tsuji et al., 1992); CVFb (Jungi and McGregor, 1979); M5 (Chen and Rael, 1997).

The term "complement-associated eye condition" is used in the broadest sense and includes all eye conditions the pathology of which involves complement, including the classical and the alternative pathways, and in particular the alternative pathway of complement. Complement-associated eye conditions include, without limitation, Chronic open-angle glaucoma, acute closed angle glaucoma, macular degenerative diseases, such as all stages of age-related macular degeneration (AMD), including dry and wet (non-exudative and exudative) forms, choroidal neovascularization (CNV), uveitis, diabetic and other ischemia-related retinopathies, and other intraocular neovascular diseases, such as diabetic macular edema, pathological myopia, von Hippel-Lindau disease, histoplasmosis of the eye, Central Retinal Vein Occlusion (CRVO), corneal neovascularization, retinal neovascularization, Leber's hereditary optic neuropathy, optic neuritis, Behcet's retinopathy, ischemic optic neuropathy, retinal vasculitis, ANCA vasculitis, Purtscher retinopathy, Sjogren's dry eye disease, dry AMD, sarcoidosis, temporal arteritis, polyarteritis *nodosa*, and multiple sclerosis.

A preferred group of complement-associated eye conditions includes age-related macular degeneration (AMD), including non-exudative (wet) and exudative (dry or atrophic) AMD, choroidal neovascularization (CNV), diabetic retinopathy (DR), and endophthalmitis.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g., bispecific antibodies) formed from at least two intact antibodies, and antibody fragments so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., Basic and Clinical Immunology, 8th Ed., Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("κ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, $4^{th}$ ed. (W.B. Saunders Co., 2000).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" molecule or cell is a molecule or a cell that is identified and separated from at least one contaminant molecule or cell with which it is ordinarily associated in the environment in which it was produced. Preferably, the isolated molecule or cell is free of association with all components associated with the production environment. The isolated molecule or cell is in a form other than in the form or setting in which it is found in nature. Isolated molecules therefore are distinguished from molecules existing naturally in cells; isolated cells are distinguished from cells existing naturally in tissues, organs, or individuals. In some embodiments, the isolated molecule is an anti-C1q antibody Fab fragment of the present disclosure. In other embodiments, the isolated cell is a host cell or hybridoma cell producing an anti-C1q antibody Fab fragment of the present disclosure.

An "isolated" antibody is one that has been identified, separated and/or recovered from a component of its production environment (e.g., naturally or recombinantly). Preferably, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by a process including at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991) (also referred to herein as Kabat 1991); by Chothia et al., J. Mol. Biol. 196:901-917 (1987) (also referred to herein as Chothia 1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues, which encompass the CDRs, as defined by each of the above cited references are set forth below in Table (X) as a comparison. The CDRs listed in Table (X) were defined in accordance with Kabat 1991.

As used herein, the terms "CDR-L1", "CDR-L2", and "CDR-L3" refer, respectively, to the first, second, and third CDRs in a light chain variable region. As used herein, the terms "CDR-H1", "CDR-H2", and "CDR-H3" refer, respectively, to the first, second, and third CDRs in a heavy chain variable region. As used herein, the terms "CDR-1", "CDR-2", and "CDR-3" refer, respectively, to the first, second and third CDRs of either chain's variable region.

The term "monoclonal antibody" as used herein refers to an antibody obtained from a population of substantially homogeneous antibodies, i.e., the individual antibodies of the population are identical except for possible naturally occurring mutations and/or post-translation modifications (e.g., isomerizations, amidations) that may be present in minor amounts.

Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., Nature, 256:495-97 (1975); Hongo et al., Hybridoma, 14 (3):253-260 (1995), Harlow et al., Antibodies: A Laboratory Manual, (Cold Spring Harbor Laboratory Press, 2d ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352:624-628 (1991); Marks et al., J. Mol. Biol. 222:581-597 (1992); Sidhu et al., J. Mol. Biol. 338(2): 299-310 (2004); Lee et al., J. Mol. Biol. 340(5):1073-1093 (2004); Fellouse, Proc. Nat'l Acad. Sci. USA 101(34): 12467-472 (2004); and Lee et al., J. Immunol. Methods 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Nat'l Acad. Sci. USA 90:2551 (1993); Jakobovits et al., Nature 362:255-258 (1993); Bruggemann et al., Year in Immunol. 7:33 (1993); U.S. Pat. Nos. 5,545,807; 5,545,806; 5,569,825; 5,625,126; 5,633, 425; and U.S. Pat. No. 5,661,016; Marks et al., Bio/Technology 10:779-783 (1992); Lonberg et al., Nature 368:856-859 (1994); Morrison, Nature 368:812-813 (1994); Fishwild et al., Nature Biotechnol. 14:845-851 (1996); Neuberger, Nature Biotechnol. 14:826 (1996); and Lonberg and Huszar, Intern. Rev. Immunol. 13:65-93 (1995).

The terms "full-length antibody," "intact antibody" and "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')2 and Fv fragments; diabodies; linear antibodies (see U.S. Pat. No. 5,641,870, Example 2; Zapata et al., Protein Eng. 8(10):1057-1062 (1995)); single-chain antibody molecules and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments with hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. (see, e.g., M. Daëron, Annu. Rev. Immunol. 15:203-234 (1997)). FcRs are reviewed in Ravetch and Kinet, Annu. Rev. Immunol. 9:457-92 (1991); Capel et al., Immunomethods 4:25-34 (1994); and de Haas et al., J. Lab. Clin. Med. 126: 330-41 (1995). Other FcRs, including those to be identified in the future, are encompassed by the term "FcR" herein. FcRs can also increase the serum half-life of antibodies.

Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants with improved or diminished binding to FcRs. See also, e.g., Shields et al., J. Biol. Chem. 9(2):6591-6604 (2001).

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Plückthun in *The Pharmacology of Monoclonal Antibodies*, vol. 113, Rosenburg and Moore eds., Springer-Verlag, New York, pp. 269-315 (1994).

"Functional fragments" of antibodies comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., Proc. Nat'l Acad. Sci. USA 90:6444-48 (1993).

As used herein, a "chimeric antibody" refers to an antibody (immunoglobulin) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Nat'l Acad. Sci. USA, 81:6851-55 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is one that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227: 381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol. 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Nat'l Acad. Sci. USA, 103:3557-3562 (2006) regarding human antibodies generated via a human B-cell hybridoma technology.

The term "hypervariable region," "HVR," or "HV," when used herein refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu in Methods in Molecular Biology 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., Nature 363:446-448 (1993) and Sheriff et al., Nature Struct. Biol. 3:733-736 (1996).

A number of HVR delineations are in use and are encompassed herein. The HVRs that are Kabat complementarity-determining regions (CDRs) are based on sequence variability and are the most commonly used (Kabat et al., supra). Chothia refers instead to the location of the structural loops (Chothia and Lesk J. Mol. Biol. 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact |
| --- | --- | --- | --- | --- |
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

The phrase "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see United States Patent Publication No. 2010-280227).

An "acceptor human framework" as used herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or fewer, 9 or fewer, 8 or fewer, 7 or fewer, 6 or fewer, 5 or fewer, 4 or fewer, 3 or fewer, or 2 or fewer. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra.

An "amino-acid modification" at a specified position refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., Bio/Technology 10:779-783 (1992) describes affinity maturation by VH- and VL-domain shuffling. Random mutagenesis of HVR and/or framework residues is described by, for example: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

As use herein, the term "specifically recognizes" or "specifically binds" refers to measurable and reproducible interactions such as attraction or binding between a target and an antibody that is determinative of the presence of the target in the presence of a heterogeneous population of molecules including biological molecules. For example, an antibody that specifically or preferentially binds to a target or an epitope is an antibody that binds this target or epitope with greater affinity, avidity, more readily, and/or with greater duration than it binds to other targets or other epitopes of the target. It is also understood that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6$ $M^{-1}$, in other instances about $10^6$ $M^{-1}$ or $10^7$ $M^{-1}$, about $10^8$ $M^{-1}$ to $10^9$ $M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, an "interaction" between a complement protein and a second protein encompasses, without limitation, protein-protein interaction, a physical interaction, a chemical interaction, binding, covalent binding, and ionic binding. As used herein, an antibody "inhibits interaction" between two proteins when the antibody disrupts, reduces, or completely eliminates an interaction between the two proteins. An antibody of the present disclosure, or fragment thereof, "inhibits interaction" between two proteins when the antibody or fragment thereof binds to one of the two proteins.

A "blocking" antibody, an "antagonist" antibody, an "inhibitory" antibody, or a "neutralizing" antibody is an antibody that inhibits or reduces one or more biological activities of the antigen it binds, such as interactions with one or more proteins. In some embodiments, blocking antibodies, antagonist antibodies, inhibitory antibodies, or "neutralizing" antibodies substantially or completely inhibit one or more biological activities or interactions of the antigen.

Antibody "effector functions" refer to those biological activities attributable to the Fc region (a native sequence Fc region or amino acid sequence variant Fc region) of an antibody, and vary with the antibody isotype.

As used herein, the term "affinity" refers to the equilibrium constant for the reversible binding of two agents (e.g., an antibody and an antigen) and is expressed as a dissociation constant ($K_D$). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. A subject anti-C1s antibody binds specifically to an epitope within a complement C1s protein. "Specific binding" refers to binding with an affinity of at least about $10^{-7}$ M or greater, e.g., $5 \times 10^{-7}$ M, $10^{-8}$ M, $5 \times 10^{-8}$ M, and greater. "Non-specific binding" refers to binding with an affinity of less than about $10^{-7}$ M, e.g., binding with an affinity of $10^{-6}$ M, $10^{-5}$ M, $10^{-4}$ M, etc.

The term "$k_{on}$", as used herein, is intended to refer to the rate constant for association of an antibody to an antigen.

The term "$k_{off}$", as used herein, is intended to refer to the rate constant for dissociation of an antibody from the antibody/antigen complex.

The term "$K_D$", as used herein, is intended to refer to the equilibrium dissociation constant of an antibody-antigen interaction.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full length of the sequences being compared.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples, and cellular samples.

An "isolated" nucleic acid molecule is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acids encoding any polypeptides and antibodies herein that exist naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors useful in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO, or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or aralkyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "about" as used herein refers to the usual error range for the respective value readily known to the skilled person in this technical field. Reference to "about" a value or parameter herein includes (and describes) embodiments that are directed to that value or parameter per se.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

Methods of Treatment

The methods of the invention provide for modulating the immune response to diseases disclosed herein through administering agents that are antagonists of complement. For example, without being bound by theory, immature astrocytes induce expression of C1q proteins in neurons during development Inflammatory mediators such as complement factor are normally expressed at very low levels in healthy brain tissue but can be rapidly induced by a variety of insults to the brain such as infection, ischaemia, and injury. Activation of C1q, C1r, and C1s contributes to the inflammatory response, which leads to synaptic loss, along with the generation and recurrence of seizures and seizure-related neuronal damage. During the developmental process of neurodegenerative disease, overexpression of C1q, C1r, and C1s may be coupled with a signal for complement activation, e.g., β-amyloid, APP, cytokines such as IFNγ, TNFα, and the like, also resulting in inflammation.

By administering agents that inhibit complement activation, synapses can be maintained that would otherwise be lost. Such agents include an anti-C1q antibody Fab fragment inhibitor, agents that upregulate expression of native complement inhibitors, agents that down-regulate C1q, C1r, or C1s synthesis in neurons, agents that block complement activation, agents that block the signal for complement activation, and the like.

The methods promote improved maintenance of neuronal function in conditions associated with synapse loss. The maintenance of neural connections provides for functional improvement in neurodegenerative disease relative to untreated patients. The prevention of synapse loss may comprise at least a measurable improvement relative to a control lacking such treatment over the period of 1, 2, 3, 4, 5, 6 days or at least one week, for example at least a 10% improvement in the number of synapses, at least a 20% improvement, at least a 50% improvement, or more.

Preferably, the agents of the present invention are administered at a dosage that decreases synapse loss while minimizing any side-effects. It is contemplated that compositions will be obtained and used under the guidance of a physician for in vivo use. The dosage of the therapeutic formulation will vary widely, depending upon the nature of the disease, the frequency of administration, the manner of administration, the clearance of the agent from the host, and the like.

The effective amount of a therapeutic composition to be given to a particular patient will depend on a variety of factors, several of which will be different from patient to patient. Utilizing ordinary skill, the competent clinician will be able to tailor the dosage of a particular therapeutic or imaging composition in the course of routine clinical trials.

Therapeutic agents, e.g., inhibitors of complement, activators of gene expression, etc. can be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intrathecal, nasal, intracheal, etc., administration. The active agent may be systemic after administration or may be localized by the use of regional administration, intramural administration, or use of an implant that acts to retain the active dose at the site of implantation.

For example, one strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents is also an option. A BBB disrupting agent can be co-administered with the therapeutic compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB is by intrathecal delivery of therapeutics or imaging agents directly to the cranium, as through an Ommaya reservoir.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g. intravascular (intravenous, intra-arterial, intracapillary) administration, injection into the cerebrospinal fluid, intracavity or direct injection in the brain. Intrathecal administration may be carried out through the use of an Ommaya reservoir, in accordance with known techniques. (F. Balis et al., Am J. Pediatr. Hematol. Oncol. 11, 74, 76 (1989).

Where the therapeutic agents are locally administered in the brain, one method for administration of the therapeutic compositions of the invention is by deposition into or near the site by any suitable technique, such as by direct injection (aided by stereotaxic positioning of an injection syringe, if necessary) or by placing the tip of an Ommaya reservoir into a cavity, or cyst, for administration. Alternatively, a convection-enhanced delivery catheter may be implanted directly into the site, into a natural or surgically created cyst, or into the normal brain mass. Such convection-enhanced pharmaceutical composition delivery devices greatly improve the diffusion of the composition throughout the brain mass. The implanted catheters of these delivery devices utilize high-flow microinfusion (with flow rates in the range of about 0.5 to 15.0 μl/minute), rather than diffusive flow, to deliver the therapeutic composition to the brain and/or tumor mass. Such devices are described in U.S. Pat. No. 5,720,720, incorporated fully herein by reference.

The effective amount of a therapeutic composition to be given to a particular patient will depend on a variety of factors, several of which will be different from patient to patient. A competent clinician will be able to determine an effective amount of a therapeutic agent to administer to a patient. Dosage of the agent will depend on the treatment, route of administration, the nature of the therapeutics, sensitivity of the patient to the therapeutics, etc. Utilizing LD50 animal data, and other information, a clinician can determine the maximum safe dose for an individual, depending on the route of administration. Utilizing ordinary skill, the competent clinician will be able to optimize the dosage of a particular therapeutic composition in the course of routine clinical trials. The compositions can be administered to the subject in a series of more than one administration. For therapeutic compositions, regular periodic administration will sometimes be required, or may be desirable. Therapeutic regimens will vary with the agent; for example, some agents may be taken for extended periods of time on a daily or semi-daily basis, while more selective agents may be administered for more defined time courses, e.g., one, two three or more days, one or more weeks, one or more months, etc., taken daily, semi-daily, semi-weekly, weekly, etc.

Formulations may be optimized for retention and stabilization in the brain. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc., in order to achieve an increase in molecular weight.

Other strategies for increasing retention include the entrapment of the agent in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e., having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

Compound Screening

In some embodiments, candidate agents are screened for the ability to modulate synapse loss, which agents may include candidate complement inhibitors, variants, fragments, mimetics, agonists and antagonists. Such compound screening may be performed using an in vitro model, a genetically altered cell or animal, or purified protein. A wide variety of assays may be used for this purpose. In one embodiment, compounds that are predicted to be antagonists or agonists of complement, including specific complement proteins, e.g., C1q, and complement activating signals, e.g. amyloid, APP, etc. are tested in an in vitro culture system, [as described below.]

For example, candidate agents may be identified by known pharmacology, by structure analysis, by rational drug design using computer based modeling, by binding assays, and the like. Various in vitro models may be used to determine whether a compound binds to, or otherwise affects complement activity. Such candidate compounds are used to contact neurons in an environment permissive for synapse loss. Such compounds may be further tested in an in vivo model for an effect on synapse loss.

Screening may also be performed for molecules produced by astrocytes, e.g., immature astrocytes, which induce C1q expression in neurons. In such assays, co-cultures of neurons and astrocytes are assessed for the production or expression of molecules that induce C1q expression. For example, blocking antibodies may be added to the culture to determine the effect on induction of C1q expression in neurons.

Synapse loss is quantitated by administering the candidate agent to neurons in culture, and determining the presence of synapses in the absence or presence of the agent. In one embodiment of the invention, the neurons are a primary culture, e.g., of retinal ganglion cells (RGCs). Purified populations of RGCs are obtained by conventional methods, such as sequential immunopanning. The cells are cultured in suitable medium, which will usually comprise appropriate growth factors, e.g., CNTF; BDNF; etc. The neural cells, e.g., RCGs, are cultured for a period of time sufficient allow robust process outgrowth and then cultured with a candidate agent for a period of about 1 day to 1 week. In some embodiments, the neurons are cultured on a live astrocyte cell feeder in order to induce signaling for synapse loss. Methods of culturing astrocyte feeder layers are known in the art. For example, cortical glia can be plated in a medium that does not allow neurons to survive, with removal of non-adherent cells.

For synapse quantification, cultures are fixed, blocked and washed, then stained with antibodies specific synaptic proteins, e.g., synaptotagmin, etc. and visualized with an appropriate reagent, as known in the art. Analysis of the staining may be performed microscopically. In one embodiment, digital images of the fluorescence emission are with a camera and image capture software, adjusted to remove unused portions of the pixel value range and the used pixel values adjusted to utilize the entire pixel value range. Corresponding channel images may be merged to create a color (RGB) image containing the two single-channel images as individual color channels. Co-localized puncta can be identified using a rolling ball background subtraction algorithm to remove low-frequency background from each image channel. Number, mean area, mean minimum and maximum pixel intensities, and mean pixel intensities for all synaptotagmin, PSD-95, and colocalized puncta in the image are recorded and saved to disk for analysis.

The term "agent" as used herein describes any molecule, e.g., protein or pharmaceutical, with the capability of modulating synapse loss, particularly through the complement pathway. In a preferred embodiment, the agent is an anti-C1q antibody Fab fragment. Candidate agents also include genetic elements, e.g., anti-sense and RNAi molecules to inhibit C1q expression, and constructs encoding complement inhibitors, e.g., CD 59, and the like. Candidate agents encompass numerous chemical classes, though typically they are organic molecules, including small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Generally a plurality of assay mixtures are run in parallel with different agent concentrations to obtain a differential response to the various concentrations. Typically one of these concentrations serves as a negative control, i.e. at zero concentration or below the level of detection.

Conditions of Interest

By "neurological" or "cognitive" function as used herein, it is meant that the decrease of synapses in the brain enhances the patient's ability to think, function, etc. As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender.

Among the conditions of interest for the present methods of inhibiting synapse loss are included a variety of neurodegenerative conditions, e.g., Alzheimer's disease, Down syndrome, Huntington's disease, amyotrophic lateral sclerosis, multiple sclerosis, myotonic dystrophy, glaucoma, Parkinson's disease; and the like. Also included are complement-associated eye conditions, such as choroidal neovascularization (CNV) and age-related macular degeneration (AMD). Such conditions benefit from administration of inhibitors of complement, including inhibitors of C1q, which allow maintenance, or reduced loss, of synapses. In some instances, where there has been neuronal loss, it may be desirable to enhance neurogenesis as well, e.g. through administration of agents or regimens that increase neurogenesis, transplantation of neuronal progenitors, etc. Agents that enhance synaptogenesis, such as thrombospondins, may also be administered.

Other conditions of interest are autoimmune conditions or complement-mediated eye conditions.

Age-related Macular Degeneration (AMD) is the leading cause of blindness in the elderly worldwide. AMD is characterized by a progressive loss of central vision attributable to degenerative and neovascular changes in the macula, a highly specialized region of the ocular retina responsible for fine visual acuity. Recent estimates indicate that 14 million persons are blind or severely visually impaired because of AMD. The disease has a tremendous impact on the physical and mental health of the geriatric population and their families and is becoming a major public health burden. New discoveries, however, are beginning to provide a clearer picture of the relevant cellular events, genetic factors, and biochemical processes associated with early AMD and how AMD is a complement-associated eye condition. Two types of AMD exist, non-exudative (dry) and exudative (wet) AMD. The dry, or nonexudative, form involves atrophic and hypertrophic changes in the retinal pigment epithelium (RPE) underlying the central retina (macula) as well as deposits (drusen) on the RPE. Patients with nonexudative AMD can progress to the wet, or exudative, form of AMD, in which abnormal blood vessels called choroidal neovascular membranes (CNVMs) develop under the retina, leak fluid and blood, and ultimately cause a blinding disciform scar in and under the retina. Nonexudative AMD, which is usually a precursor of exudative AMD, is more common. The presentation of nonexudative AMD varies; hard drusen, soft drusen, RPE geographic atrophy, and pigment clumping can be present. Complement components are deposited on the RPE early in AMD and are major constituents of drusen.

Alzheimer's disease is a progressive, inexorable loss of cognitive function associated with an excessive number of senile plaques in the cerebral cortex and subcortical gray matter, which also contains—amyloid and neurofibrillary tangles consisting of tau protein. The common form affects persons >60 yr old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus caeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

Amyotrophic lateral sclerosis (ALS) is a rapidly progressive, invariably fatal neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 yr; 50% die within 3 yr of onset, 20% live 5 yr, and 10% live 10 yr. Diagnostic features include onset during middle or late adult life and progressive, generalized motor involvement without sensory abnormalities. Nerve conduction velocities are normal until late in the disease.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Preventing synapse loss may maintain neuron function in these patients.

Down Syndrome is a chromosomal disorder usually resulting in mental retardation, a characteristic facies, and many other typical features, including microcephaly and short stature. In about 95% of cases, there is an extra whole chromosome 21. At autopsy, adult Down syndrome brains show the typical microscopic findings of Alzheimer's disease, and many persons also develop the associated clinical signs.

Parkinson's Disease is an idiopathic, slowly progressive, degenerative CNS disorder characterized by slow and decreased movement, muscular rigidity, resting tremor, and postural instability. In primary Parkinson's disease, the pigmented neurons of the substantia nigra, locus caeruleus, and other brain stem dopaminergic cell groups are lost. The cause is not known. The loss of substantia nigra neurons, which project to the caudate nucleus and putamen, results in depletion of the neurotransmitter dopamine in these areas. Onset is generally after age 40, with increasing incidence in older age groups.

Secondary parkinsonism results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including striatonigral degeneration.

Myotonic dystrophy is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (e.g., diabetes mellitus). Mental retardation is common. Severely affected persons die by their early 50s.

Glaucoma is a common neurodegenerative disease that affects retinal ganglion cells (RGCs). Substantial effort is being expended to determine how RGCs die in glaucoma. Evidence supports the existence of compartmentalized degeneration programs in synapses and dendrites, including RGCs. Recent data, from in vitro studies and from an inherited mouse model of glaucoma, suggest that molecularly distinct degenerative pathways underlie the destruction of RGC somata and RGC axons. In various neurodegenerative diseases, axons, dendrites and synapses often degenerate well before the cells die, and there is increasing evidence that this is important for the production of clinical symptoms and signs.

Huntington's disease (HD) is a hereditary progressive neurodegenerative disorder characterized by the development of emotional, behavioral, and psychiatric abnormalities; loss of previously acquired intellectual or cognitive functioning; and movement abnormalities (motor disturbances). The classic signs of HD include the development of chorea—or involuntary, rapid, irregular, jerky movements that may affect the face, arms, legs, or trunk—as well as the gradual loss of thought processing and acquired intellectual abilities (dementia). There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

Multiple Sclerosis is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

The methods of the invention can find use in combination with cell or tissue transplantation to the central nervous system, where such grafts include neural progenitors such as those found in fetal tissues, neural stem cells, embryonic stem cells or other cells and tissues contemplated for neural repair or augmentation. Neural stem/progenitor cells have been described in the art, and their use in a variety of therapeutic protocols has been widely discussed. For example, inter alia, U.S. Pat. No. 6,638,501, Bjornson et al.; U.S. Pat. No. 6,541,255, Snyder et al.; U.S. Pat. No. 6,498,018, Carpenter; U.S. Patent Application 20020012903, Goldman et al.; Palmer et al. (2001) Nature 411 (6833):42-3; Palmer et al. (1997) Mol Cell Neurosci. 8(6):389-404; Svendsen et al. (1997) Exp. Neurol. 148(1):135-46 and Shihabuddin (1999) Mol Med Today. 5(11):474-80; each herein specifically incorporated by reference.

Neural stem and progenitor cells can participate in aspects of normal development, including migration along well-established migratory pathways to disseminated CNS regions, differentiation into multiple developmentally- and regionally-appropriate cell types in response to microenvironmental cues, and non-disruptive, non-tumorigenic interspersion with host progenitors and their progeny. Human NSCs are capable of expressing foreign transgenes in vivo in these disseminated locations. A such, these cells find use in the treatment of a variety of conditions, including traumatic injury to the spinal cord, brain, and peripheral nervous system; treatment of degenerative disorders including Alzheimer's disease, Huntington's disease, Parkinson's disease; affective disorders including major depression; stroke; and the like. By synapse loss enhancers, the functional connections of the neurons are enhances, providing for an improved clinical outcome.

Pharmaceutical Compositions

The antibody Fab fragments of the present invention may be administered for the treatment of complement-associates eye conditions in the form of pharmaceutical compositions. Therapeutic formulations of an antibody Fab fragment of the invention, are prepared for storage by mixing the antibody Fab fragment having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Lipofections or liposomes can also be used to deliver the antibody Fab fragment into cell, wherein the smallest fragment which specifically binds to the binding domain of the target protein is preferred.

The antibody Fab fragment may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody Fab fragment, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

The compounds of the invention for prevention or treatment of an ocular disease or condition are typically administered by ocular, intraocular, and/or intravitreal injection. Other methods administration by also be used, which includes but is not limited to, topical, parenteral, subcutaneous, intraperitoneal, intrapulmonary, intranasal, and intralesional administration. Parenteral infusions include intramuscular, intravenous, intra-arterial, intraperitoneal, or subcutaneous administration.

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as AMD and CNV, is direct intravitreal injection. Intravitreal injections are usually repeated at intervals which depend on the patient's condition, and the properties and half-life of the drug delivered. For intraocular (e.g., intravitreal) penetration, usually molecules of smaller size are preferred.

The efficacy of the treatment of complement-associated eye conditions, such as AMD or CNV, can be measured by various endpoints commonly used in evaluating intraocular diseases. For example, vision loss can be assessed. Vision loss can be evaluated by, but not limited to, e.g., measuring by the mean change in best correction visual acuity (BCVA) from baseline to a desired time point (e.g., where the BCVA is based on Early Treatment Diabetic Retinopathy Study (ETDRS) visual acuity chart and assessment at a test distance of 4 meters), measuring the proportion of subjects who lose fewer than 15 letters in visual acuity at a desired time point compared to baseline, measuring the proportion of subjects who gain greater than or equal to 15 letters in visual acuity at a desired time point compared to baseline, measuring the proportion of subjects with a visual-acuity Snellen equivalent of 20/2000 or worse at a desired time point, measuring the NEI Visual Functioning Questionnaire, measuring the size of CNV and amount of leakage of CNV at a desired time point, e.g., by fluorescein angiography, etc. Ocular assessments can be done, e.g., which include, but are not limited to, e.g., performing eye exam, measuring intraocular pressure, assessing visual acuity, measuring slit-lamp pressure, assessing intraocular inflammation, etc.

Nucleic Acids, Vectors and Host Cells

Antibody Fab fragments of the present disclosure may be produced using recombinant methods and compositions, e.g., as described in U.S. Pat. No. 4,816,567. In some embodiments, isolated nucleic acids having a nucleotide sequence encoding any of the antibody Fab fragments of the present disclosure are provided. Such nucleic acids may encode an amino acid sequence containing the $V_L/C_L$ and/or an amino acid sequence containing the $V_H/C_H1$ of the anti-C1q antibody. In some embodiments, one or more vectors (e.g., expression vectors) containing such nucleic acids are provided. In some embodiments, a host cell containing such nucleic acid is also provided. In some embodiments, the host cell contains (e.g., has been transduced with): (1) a vector containing a nucleic acid that encodes an amino acid sequence containing the $V_L/C_L$ of the antibody and an amino acid sequence containing the $V_H/C_H1$ of the antibody, or (2) a first vector containing a nucleic acid that encodes an amino acid sequence containing the $V_L/C_L$ of the antibody and a second vector containing a nucleic acid that encodes an amino acid sequence containing the $V_H/C_H1$ of the antibody. In some embodiments, the host cell is eukaryotic, e.g., a Chinese Hamster Ovary (CHO) cell or lymphoid cell (e.g., Y0, NS0, Sp20 cell).

Methods of making an anti-C1q antibody Fab fragment of the present disclosure are provided. In some embodiments, the method includes culturing a host cell of the present disclosure containing a nucleic acid encoding the anti-C1q antibody Fab fragment, under conditions suitable for expression of the antibody Fab fragment. In some embodiments, the antibody Fab fragment is subsequently recovered from the host cell (or host cell culture medium).

For recombinant production of a humanized anti-C1q antibody Fab fragment of the present disclosure, a nucleic acid encoding the anti-C1q antibody Fab fragment is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors containing a nucleic acid sequence encoding any of the anti-C1q antibody Fab fragment of the present disclosure, or fragments thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the nucleic acids of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding an anti-C1q antibody of the present disclosure.

Suitable host cells for cloning or expression of antibody Fab fragment-encoding vectors include prokaryotic or eukaryotic cells. For example, anti-C1q antibody Fab fragments of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523; and Charlton, Methods in Molecular Biology, Vol. 248 (B. K. C. Lo, ed., Humana Press, Totowa, N.J., 2003), pp. 245-254, describing expression of antibody fragments in E. coli.). After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross, Nat. Biotech. 22:1409-1414 (2004); and Li et al., Nat. Biotech. 24:210-215 (2006)).

Suitable host cells for the expression of glycosylated antibody Fab fragments can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants.).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Combination Treatments

The complement inhibitors of the present disclosure may be used, without limitation, conjointly with any additional treatment, such as immunosuppressive therapies, for any disease disclosed herein, including autoimmune and/or neurodegenerative diseases.

In some embodiments, the antibodies of this disclosure are administered in combination with an inhibitor of the alternative pathway of complement activation. Such inhibitors may include, without limitation, factor B blocking antibodies, factor D blocking antibodies, soluble, membrane-bound, tagged or fusion-protein forms of CD59, DAF, CR1, CR2, Crry or Comstatin-like peptides that block the cleavage of C3, non-peptide C3aR antagonists such as SB 290157, Cobra venom factor or non-specific complement inhibitors such as nafamostat mesilate (FUTHAN; FUT-175), aprotinin, K-76 monocarboxylic acid (MX-1) and heparin (see, e.g., T. E. Mollnes & M. Kirschfink, Molecular Immunology 43 (2006) 107-121). In some embodiments, the antibodies of this disclosure are administered in combination with an inhibitor of the interaction between the autoantibody and its autoantigen. Such inhibitors may include purified soluble forms of the autoantigen, or antigen mimetics such as peptide or RNA-derived mimotopes, including mimotopes of the AQP4 antigen. Alternatively, such inhibitors may include blocking agents that recognize the autoantigen and prevent binding of the autoantibody without triggering the classical complement pathway. Such blocking agents may include, e.g., autoantigen-binding RNA aptamers or antibodies lacking functional C1q binding sites in their Fc domains (e.g., Fab fragments or antibody otherwise engineered not to bind C1q).

Kits

The invention also provides kits containing antibody Fab fragments of this disclosure. Kits of the invention include one or more containers comprising a purified anti-C1q antibody Fab fragment and instructions for use in accordance with methods known in the art. Generally, these instructions comprise a description of administration of the inhibitor to treat or diagnose a disease, according to any methods known in the art. The kit may further comprise a description of selecting an individual suitable for treatment based on identifying whether that individual has the disease and the stage of the disease.

The instructions generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating a specific disease. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is an inhibitor of classical complement pathway. The container may further comprise a second pharmaceutically active agent.

Kits may optionally provide additional components such as buffers and interpretive information. Normally, the kit comprises a container and a label or package insert(s) on or associated with the container.

EXEMPLIFICATION

Example 1: C1q Binding Assay

A direct ELISA was used to assess binding of Fab and full-length antibodies to human C1q (FIG. 1). Briefly, black 96-well plates (#3925, Corning) were coated with human C1q (2 ug/mL) (Complement Technology) in Bicarbonate buffer (pH 9.4) (Thermo Scientific), overnight at 4 C. Next day the plates are washed with dPBS thrice and blocked with 3% BSA/PBS for 1 hour at room temperature (RT). Serial dilutions of M1, M1-Fab were prepared in dPBS 0.3% BSA, 0.1% Tween buffer (50 uL/well). Following incubation for 1 hour at RT, add Alkaline-phosphatase (AP) conjugated secondary antibodies to mouse kappa or mouse FC, human kappa and human FC (Jackson Immunoresearch), respectively at 2000-4000 fold. After an additional 1 hour of incubation at RT, plates are washed thrice with dPBS 0.05% Tween and luminescence developed with AP substrate (Thermo Scientific). Luminescence counts were measured using Envision plate reader (Perkin Elmer). Counts are plotted as a function of concentration and a 4-parameter logistic fit was used to derive EC50 for C1q binding. As demonstrated in FIG. 1, the M1 Fab has the same binding affinity as M1 whole antibody. FIG. 1B shows M1 whole antibody (bivalent) and M1 Fab (monovalent). It was anticipated that M1 whole antibody would exhibit higher avidity for binding to C1q than M1 antibody Fab.

Example 2: Hemolysis

Figure 2:
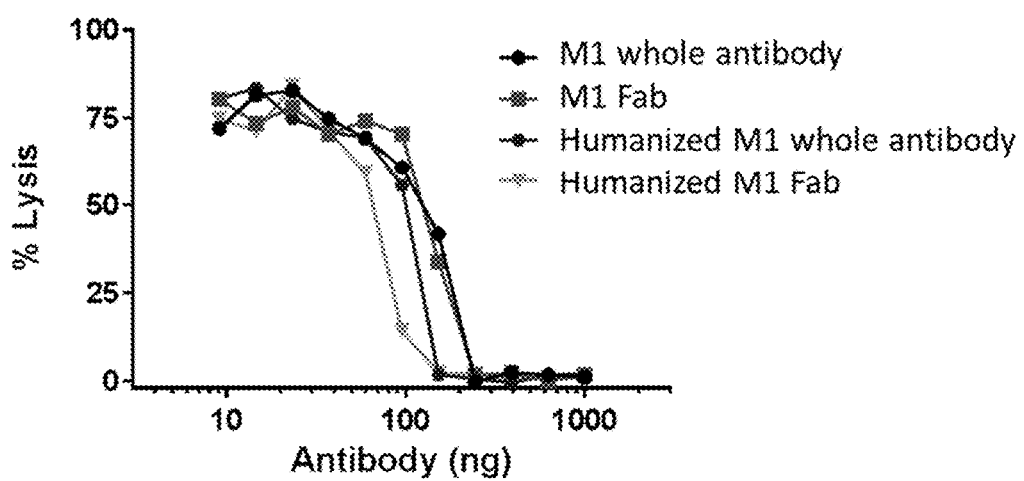
FIG. 2 shows that the M1 Fab has the same functional potency as the M1 whole antibody.

The ability of anti-C1q antibodies to inhibit RBC hemolysis was determined using sensitized sheep RBCs and normal human serum as source of complement (FIG. 2). Briefly, antibodies (M1-whole IgG, M1-Fab, Humanized M1 and Humanized M1-Fab) were titrated over a range of 10000 to 10 ng/mL in 50× diluted normal human serum in GVB++ buffer (Complement Technology). Then, 50 uL of diluted serum was mixed with 50 uL of diluted sheep RBCs (~100 million cells/mL) (Complement Technology). The samples were incubated at 37 C for 30 minutes. Then the plates were centrifuged at 2000 rpm for 5 minutes, supernatant collected and absorbance read at 415 nm. Controls were run that included—background hemolysis in GVB++ buffer alone without serum and maximal hemolysis triggered using water. The raw absorbance was background subtracted and normalized to maximal hemolysis and plotted as a function of concentration. The IC50 for inhibition of hemolysis was determined using 4 parameter logistic fits. As demonstrated in FIG. 2, M1 Fab has the same functional potency as M1 whole antibody. It was anticipated that M1 whole antibody would exhibit higher potency because of its ability to engage multiple functional head groups of C1q (FIG. 1B), and because of the larger size for stearic hindrance of other head groups.

INCORPORATION BY REFERENCE

Each of the patents, published patent applications, and non-patent references cited herein are hereby incorporated by reference in their entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inhibiting synapse loss comprising administering to a patient suffering from adverse synapse loss an antibody Fab fragment that binds to C1q, wherein the antibody Fab fragment comprises a heavy chain and a light chain, wherein the heavy chain comprises SEQ ID NO:1 and the light chain comprises SEQ ID NO:2.

2. The method of claim 1, wherein the patient has suffered synapse loss as a result of a neurodegenerative disorder, central nervous system disorder, or a peripheral nervous system disorder.

3. The method of claim 2, wherein the neurodegenerative disorder is Alzheimer's disease.

4. The method of claim 1, further comprising administration of neural progenitors, or a neurogenesis enhancer.

5. The method of claim 1, wherein the antibody Fab fragment binds to C1q and inhibits complement activation.

6. A method of treating a disease associated with C1q mediated activation of the classical complement pathway in an individual in need of such treatment, the method comprising administering an antibody Fab fragment that binds to C1q, wherein the antibody Fab fragment comprises a heavy chain and a light chain, wherein the heavy chain comprises SEQ ID NO:1 and the light chain comprises SEQ ID NO:2.

7. The method of claim 6, wherein the disease associated with C1q mediated activation of the classical complement pathway is a neurodegenerative disorder.

8. The method of claim 7, wherein the neurodegenerative disorder is associated with loss of synapses or loss nerve connections.

9. The method of claim 7, wherein the neurodegenerative disorder is associated with synapse loss that is dependent on the complement receptor 3(CR3)/C3 or complement receptor CR1.

10. The method of claim 7, wherein the neurodegenerative disorder is associated with pathological activity-dependent synaptic pruning.

11. The method of claim 7, wherein the neurodegenerative disorder is associated with synapse phagocytosis by microglia.

12. The method of claim 7, wherein the neurodegenerative disorder is selected from Alzheimer's disease, amyotrophic lateral sclerosis, multiple sclerosis, glaucoma, myotonic dystrophy, Guillain-Barre' syndrome (GBS), Myasthenia Gravis, Bullous Pemphigoid, spinal muscular atrophy, Down syndrome, Parkinson's disease, or Huntington's disease.

13. The method of claim 6, wherein the disease associated with C1q mediated activation of the classical complement pathway is an inflammatory disease, autoimmune disease, complement-associated eye disease or metabolic disorder.

14. The method of claim 13, wherein the inflammatory disease, autoimmune disease, complement-associated eye disease or metabolic disorder is selected from diabetes, obesity, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulinemia, antiphospholipid syndrome, Chronic open-angle glaucoma, acute closed angle glaucoma, macular degenerative diseases, age-related macular degeneration (AMD), geographic atrophy, choroidal neovascularization (CNV), uveitis, diabetic retinopathy, ischemia-related retinopathy, endophthalmitis, intraocular neovascular disease, diabetic macular edema, pathological myopia, von Hippel-Lindau disease, histoplasmosis of the eye, Neuromyelitis Optica (NMO), Central Retinal Vein Occlusion (CRVO), corneal neovascularization, retinal neovascularization, Leber's hereditary optic neuropathy, optic neuritis, Behcet's retinopathy, ischemic optic neuropathy, retinal vasculitis, ANCA vasculitis, Purtscher retinopathy, Sjogren's dry eye disease, dry AMD, sarcoidosis, temporal arteritis, polyarteritis nodosa, multiple sclerosis, allo-transplantation, hyperacute rejection, hemodialysis, chronic occlusive pulmonary distress syndrome (COPD), asthma, aspiration pneumonia, multiple sclerosis, Guillain-Barre syndrome, Myasthenia Gravis, Bullous Pemphigoid, or myositis.

15. The method of claim 6, wherein the disease associated with C1q mediated activation of the classical complement pathway is an autoimmune disease selected from myasthenia gravis, Diabetes mellitus type 1, Hashimoto's thyroiditis, Addison's disease, Coeliac disease, Crohn's disease, pernicious anaemia, Pemphigus vulgaris, vitiligo, autoimmune hemolytic anemias, paraneoplastic syndromes, a vasculitis disease, hypocomplementemic urticarial vasculitis (HUV), polymyalgia rheumatica, temporal arteritis, Wegener's granulomatosis, multiple sclerosis, Guillain-Barre syndrome, Myasthenia Gravis, Bullous Pemphigoid, or myositis.

16. The method of claim 1, wherein the antibody Fab fragment has a dissociation constant ($K_D$) for mouse C1q in the range of from 1 pM to 200 pM.

17. The method of claim 1, wherein the antibody Fab fragment is humanized.

18. The method of claim 6, wherein the antibody Fab fragment has a dissociation constant ($K_D$) for mouse $C_1q$ in the range of from 1 pM to 200 pM.

19. The method of claim 6, wherein the antibody Fab fragment is humanized.

* * * * *

SEQUENCE LISTING

<160> NUMBER OF SEQ ID NOS: 12

<210> SEQ ID NO 1
<211> LENGTH: 229

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Leu Lys Lys Pro Gly Ala
1               5                   10                  15

Ser Val Lys Val Ser Cys Lys Ser Ser Gly Tyr His Phe Thr Ser Tyr
            20                  25                  30

Trp Met His Trp Val Lys Gln Ala Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr
225

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Val Gln Ile Thr Gln Ser Pro Ser Ser Leu Ser Ala Ser Leu Gly
1               5                   10                  15

Glu Arg Ala Thr Ile Asn Cys Arg Ala Ser Lys Ser Ile Asn Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

Glu Asp Phe Ala Met Tyr Tyr Cys Gln Gln His Asn Glu Tyr Pro Leu
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
caggtgcagc tggtgcagtc aggggctgag ctgaagaagc ctggggcttc agtgaaggtt      60
tcctgcaagt cttctggcta ccatttcacc agctactgga tgcactgggt gaagcaggcc     120
cctggacaag gccttgagtg gattggagtg attcatccta atagtggtag tattaactac     180
aatgagaagt tcgagagcag agtcacaatt actgtagaca atccaccag cacagcctac      240 atggagctca gcagcctgag atctgaggac acggcggtct attattgtgc aggagagaga     300
gattctacgg aggttctccc tatggactac tggggtcaag aaccacggt caccgtctcc      360 tcagcgtcca ccaaaggccc gtccgtgttt ccgctggcgc gtcctccaa atccacctcc      420 ggcggcaccg cggcgctggg ctgcctggtg aaagattatt ttccggaacc ggtgaccgtg     480
tcctggaatt ccggcgcgct gacctccggc gtgcatacct ttccggcggt gctgcagtcc    540
tccggcctgt attccctgtc ctccgtggtg accgtgccgt cctcctccct gggcacccag     600
acctatattt gcaatgtgaa tcataaaccg tccaatacca agtggataa aaaagtggaa      660 ccgaaatcct gcgataaaac ccatacc                                        687

<210> SEQ ID NO 4
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gatgtccaga tcacacagtc tccatcttcc ctttctgcat ctctcggaga aagagctact      60
attaattgca gggcaagtaa gagcattaac aaatacttag cctggtatca acagaaacct    120
gggaaagctc ctaagctcct tatctactct ggctccactt tgcaatctgg aattccagca    180

-continued

```
aggttcagtg gcagtggatc tggtacagat ttcactctca ccatcagtag cctggagcct    240
gaagattttg caatgtatta ctgtcaacaa cataatgaat acccgctcac gttcggtcag    300
gggaccaagc tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacc ctgacg    540 ctgagcaaag cagactacga gaaacacaaa gtctacgcct gcgaagtcac ccatcagggc    600
ctgagctcgc ccgtcacaaa gagcttcaac aggggagagt gttag               645
```

<210> SEQ ID NO 5
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Gln Ser Gly Ala Glu Leu Lys Lys Pro Gly Ala
1               5                   10                  15

Ser Val Lys Val Ser Cys Lys Ser Ser Gly Tyr His Phe Thr Ser Tyr
            20                  25                  30

Trp Met His Trp Val Lys Gln Ala Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Lys Ala Thr Ile Thr Val Asp Lys Ser Thr Ser Thr Ala Tyr
65                  70                  75                  80

Met Gln Leu Ser Ser Leu Thr Ser Glu Asp Ser Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Ser Val Thr Val Ser Ser
        115                 120

<210> SEQ ID NO 6
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Val Gln Ser Gly Ala Glu Leu Lys Lys Pro Gly Ala
1               5                   10                  15

Ser Val Lys Val Ser Cys Lys Ser Ser Gly Tyr His Phe Thr Ser Tyr
            20                  25                  30

Trp Met His Trp Val Lys Gln Ala Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Arg Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Thr Val Thr Val Ser Ser
        115                 120

<210> SEQ ID NO 7
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Leu Lys Lys Pro Gly Ala
1               5                   10                  15

Ser Val Lys Val Ser Cys Lys Ser Ser Gly Tyr His Phe Thr Ser Tyr
            20                  25                  30

Trp Met His Trp Val Lys Gln Ala Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Thr Val Thr Val Ser Ser
        115                 120

<210> SEQ ID NO 8
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Gln Ser Gly Ala Glu Leu Lys Lys Pro Gly Ala
1               5                   10                  15

Ser Val Lys Val Ser Cys Lys Ser Ser Gly Tyr His Phe Thr Ser Tyr
            20                  25                  30

Trp Met His Trp Val Arg Gln Ala Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Thr Val Thr Val Ser Ser
        115                 120

<210> SEQ ID NO 9

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Val Gln Ile Thr Gln Ser Pro Ser Tyr Leu Ala Ala Ser Leu Gly
1               5                   10                  15

Glu Arg Ala Thr Ile Asn Cys Arg Ala Ser Lys Ser Ile Asn Lys Tyr
            20                  25                  30

Leu Ala Trp Tyr Gln Gln Lys Pro Gly Lys Thr Asn Lys Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Gln Gly Thr Lys Leu Glu Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Val Gln Ile Thr Gln Ser Pro Ser Ser Leu Ser Ala Ser Leu Gly
1               5                   10                  15

Glu Arg Ala Thr Ile Asn Cys Arg Ala Ser Lys Ser Ile Asn Lys Tyr
            20                  25                  30

Leu Ala Trp Tyr Gln Gln Lys Pro Gly Lys Ala Asn Lys Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Gln Gly Thr Lys Leu Glu Ile Lys
            100                 105

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Val Gln Ile Thr Gln Ser Pro Ser Ser Leu Ser Ala Ser Leu Gly
1               5                   10                  15

Glu Arg Ala Thr Ile Asn Cys Arg Ala Ser Lys Ser Ile Asn Lys Tyr
            20                  25                  30
```

-continued

```
Leu Ala Trp Tyr Gln Gln Lys Pro Gly Lys Ala Pro Lys Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Gln Gly Thr Lys Leu Glu Ile Lys
                100                 105

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Leu Thr Gln Ser Pro Ser Ser Leu Ser Ala Ser Leu Gly
1               5                   10                  15

Glu Arg Ala Thr Ile Asn Cys Arg Ala Ser Lys Ser Ile Asn Lys Tyr
                20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Gln Gly Thr Lys Leu Glu Ile Lys
                100                 105
```